United States Patent [19]

Holland

[11] Patent Number: 5,213,978
[45] Date of Patent: May 25, 1993

[54] **PROTEASE FROM *MICROCOCCUS SEDENTARIUS* FOR DEGRADING PROTEIN OF HUMAN CALLUS OR CORN TISSUE**

[75] Inventor: Keith T. Holland, Leeds, United Kingdom

[73] Assignee: Scholl Plc, Berkshire, England

[21] Appl. No.: 705,090

[22] Filed: May 24, 1991

[30] Foreign Application Priority Data

May 25, 1990 [GB] United Kingdom ............... 9011807

[51] Int. Cl.$^5$ .................... C12N 9/52; C12N 9/50; C12N 1/00
[52] U.S. Cl. .................... 435/220; 435/859; 435/219
[58] Field of Search ............ 435/220, 859, 219

[56] References Cited

U.S. PATENT DOCUMENTS

| | | | |
|---|---|---|---|
| 3,692,631 | 9/1972 | Larson et al. | 435/220 |
| 3,707,504 | 12/1972 | Johnson | 435/220 |
| 4,364,926 | 12/1982 | Yokogawa et al. | 435/220 |
| 4,581,332 | 4/1986 | Soejima et al. | 435/220 |

OTHER PUBLICATIONS

Kloos, et al., *Isolation and Characterization of Micrococci From Human Skin, Including Two New Species: Micrococcus Lylae and Micrococcus Kristinae*, (Int'l Journal of Systematic Bacteriology, Jan., 1974, vol. 24, No. 1 pp. 79-101).
Laemmli, *Cleavage of Structural Proteins during the Assembly of the Head of Bacteriophage T4*, (Nature, Aug. 1970, vol. 227, pp. 680-685).
Millet, *Characterization of Proteinases Excreted by Bacillus subtilis Marburg Strain during Sporulation*, (Journal of Applied Bacteriology, 1970, 33, pp. 207-219).
Schleifer et al., *The Genus Micrococcus*, (A Handbook on Habitats, Isolation and Idnetification of Bacteria, vol. 2, pp. 1539-1547).
Winter et al., *Analytical Electrofocusing in Thin Layers of Polyacrylamide Gels*, (LKB Application Note 250, Dec., 1977).
Marshall et al., *The Cutaneous Microbiology of Normal Human Feet*, (Journal of Applied Bacteriology, 1987, vol. 62, pp. 139-146).
Nordstrom et al., *Pitted Keratolysis, The Role of Micrococcus sedentarius*, (Arch Dermatol-vol. 123, Oct., 1987, pp. 1320-1325).
Marshall et al., *A Comparative Study of the Cutaneous Microflora of Normal Feet with Low and High Levels of Odour*, (Journal of Applied Bacteriology, 1988, vol. 65, pp. 61-68).
J. Marshall et al., *Micrococcus Sedentarius: The Transition from Commensal to Pathogen*, (Clinical Research, vol. 37, No. 2., p. 758A, 1989).
K. M. Nordstrom et al., *Similarities Between Dermatophilus Congolensis and Micrococcus Sedentarius*, (vol. 87, No. 0, p. 244, 1987).
K. T. Holland et al., *Qualitative and Quantitative Assay for Detection of Callus Degrading Activity by Bacteria*, (vol. 11, No. 4, pp. 224-227, 1990).
K. T. Holland et al., *The Effect of pH on the Growth of Proteinase Production of Micrococcus Sedentarius in Relation to Pitted Keratolysis*, (vol. 95, No. 4, p. 473, 1990).

*Primary Examiner*—David M. Naff
*Assistant Examiner*—Mike Meller
*Attorney, Agent, or Firm*—Sheridan, Ross & McIntosh

[57] ABSTRACT

An enzyme material isolated from a culture of *Micrococcus sedentarius* which comprises one or more proteases having an ability to degrade protein, including human callus. In one embodiment the enzyme material is water soluble, non-dialyzable through a membrane having a molecular weight cut-off of 10 kDa, has an isoelectric point of 4.6, a molecular weight of 30.3 kDa, an optimum pH for protease activity at about 8.2, and functions at an optimum temperature of about 40° C. In another embodiment, the enzyme material is water-soluble, non-dialyzable through a membrane having a molecular weight cut off of 10 kDa, has an isoelectric point of 2.7, a molecular weight of 50 kDa, an optimum pH for protease activity at about pH 10.2, and functions at an optimum temperature of about 46° C.

14 Claims, 18 Drawing Sheets

FIG. 3 Temperature optimum curves for Proteases 1 and 2

The effect of temperature on callus degradation by *M. sedentarius* protease 2 in 150 mM phosphate buffer pH 7.6.

FIG. 6 The effect of pH on callus degradation by M.sedentarius protease 1 at 40°C.

The effect of pH on callus degradation by M.sedentarius protease 2 at 50°C.

pH stability of P2 incubated at various pH values at 60°C

FIG. 10 Protease 2 pH stability at 4°C.

Effect of NaCl concentration on callus degradation by Protease 1 and 2 in Tris-HCl buffers at pH 7.1 and 7.5, respectively.

Effect of MgCl₂ concentration on callus degradation by Protease 2 in 150 mM Tris-HCl at pH 7.5

DEGRADATION OF KERATIN BY PROTEASE 1 AND CRUDE AMICON RETENTATE

1. PROTEASE 1 (2.4 PROTEASE UNITS)
2. CRUDE AMICON RETENTATE (2.4 PROTEASE UNITS)
3. NO ENZYME (CONTROL)

DEGRADATION OF KERATIN BY DOUBLING DILUTIONS OF PROTEASE 2

1. 3 PROTEASE UNITS (N)
11. 0.003 (PROTEASE UNITS) $(N/_{1024})$
12. NO ENZYME (CONTROL)

S. STANDARD MOLECULAR MASS PROTEINS

PROTEASE FROM *MICROCOCCUS SEDENTARIUS* FOR DEGRADING PROTEIN OF HUMAN CALLUS OR CORN TISSUE

FIELD OF THE INVENTION

The present invention relates to the micro-organism *Micrococcus sedentarius*, proteases, their production from *Micrococcus sedentarius* and uses thereof.

BACKGROUND OF THE INVENTION

Enzymes which digest proteins are widely distributed in nature. Both intracellular and extracellular proteases exist in a wide variety of organisms. Extracellular proteases are produced by micro-organisms to enable them to convert proteinaceous material to low molecular weight peptides for transport into the cell, to satisfy either carbon and energy requirements and/or nitrogen requirements for growth. Bacteria, fungi and yeasts are known to produce different proteases, both intracellular and extracellular, whose biochemical characteristics and properties have been described; see e.g. The Enzymes, Ed. Paul D. Boyer Vol. III "Hydrolysis: peptide bonds". 3rd Edition 1971.

We have now found it possible to produce extracellular proteases from *Micrococcus sedentarius* which are capable of solubilizing human callus material and degrading other proteinaceous material.

SUMMARY OF THE PRESENT INVENTION

The present invention is directed to an enzyme material isolated from a culture of *Micrococcus sedentarius* which comprises one or more proteases having an ability to degrade protein, and in particular, human callus or corn tissue. The present invention includes an enzyme material that is water soluble, non-dialyzable through a membrane having a molecular weight cut off of about 10 kilo Daltons (kDa), an isoelectric point of about 4.6, and a molecular weight of about 30.3 kDa and displaying optimum protease activity at a pH of about 8.2 and an optimum temperature at about 40° C. In another embodiment, the enzyme material is more particularly one having a molecular weight cut off of 10 kDa, an isoelectric point of 2.7, a molecular weight of 50 kDa and an optimum pH for protease activity at about 10.2 and at an optimum temperature at about 46° C. In a preferred embodiment, the enzyme material is obtained from *Micrococcus sedentarius* and is present in a substantially pure form.

The present invention includes enzyme material in the form of a cell free culture of *Micrococcus sedentarius* and a most preferred embodiment, the source is *Micrococcus sedentarius* NCIMB 40287.

The present invention includes a process for the preparation of enzyme material in which the enzyme material is isolated from a culture of *Micrococcus sedentarius*. The invention further includes a cell free culture of *Micrococcus sedentarius* which exhibits protease activity. Furthermore, the invention includes a process for the degradation of protein, and in particular, human callus or corn protein, in which the enzyme material is applied to the proteinaceous material to be degraded. The present enzyme material can be used as a medicament for the digestion of human callus or corn material and for pharmaceutical compositions in which the enzyme material is present with a pharmaceutically acceptable carrier or excipient. In another embodiment, the present invention includes a composition for topical application to the skin of a human subject comprising the enzyme material isolated from a culture of *Micrococcus sedentarius*, combined with a topically acceptable base.

According to one aspect of the present invention there are provided enzyme materials isolated from a culture of *Micrococcus sedentarius* which comprise one or more proteases having an ability to degrade protein, including human callus.

According to another aspect of the present invention there is provided an enzyme material having the following characteristics:
water-soluble,
non-dialyzable (through a membrane having a molecular weight
cut-off of 10 kDa),
an isoelectric point of 4.6,
a molecular weight of 30.3 kDa,
an optimum pH for protease activity at about 8.2, and
an optimum temperature at about 40° C.

The enzyme material, which may be obtained from *Micrococcus sedentarius*, has been found to have an optimum pH for human callus-degrading activity at about 7.1 and an optimum temperature at about 40° C. It has been found that at 35° C. the enzyme material has protease activity in the pH range of about 5.1 to about 10.9, and human callus-degrading activity at 40° C. in the range of about 5.9 to about 8.0.

According to a further aspect of the present invention there is provided an enzyme material having the following characteristics:
water-soluble,
non-dialyzable (through a membrane having a molecular
weight cut-off of 10 kDa),
an isoelectric point of 2.7,
a molecular weight of 50 kDa;
an optimum pH for protease activity at about pH 10.2, and
an optimum temperature at about 46° C.

This enzyme material, which also may be obtained from *Micrococcus sedentarius* has been found to have an optimum pH for callus-degrading of about 7.5 and an optimum temperature at about 50° C.

It has been found that at 35° C. the enzyme material has protease activity in the pH range of about 5.1 to about 11.3, and human callus-degrading activity at 50° C. in the range of about 4.3 to about 10.0.

According to another aspect of the present invention there is provided a process for the preparation of enzyme materials of the present invention comprising isolating the enzyme materials from a culture of *Micrococcus sedentarius*.

According to another aspect of the invention there is provided a cell-free culture of *Micrococcus sedentarius* which exhibits protease activity.

In all the above aspects, it is preferred to employ the novel strain of *Micrococcus sedentarius* (NCIMB No. 40287), deposited in accordance with the Budapest Treaty on the International Recognition of the Deposit of Microorganisms for the purpose of Patent Procedure.

According to other aspects of the present invention there are provided processes for degrading human callus or corns comprising the application of an enzyme material or cell-free culture of the present invention to human callus or corns.

According to another aspect of the present invention there is provided a process for degrading protein comprising the application of an enzyme material or cell-free culture of the present invention to protein.

According to another aspect of the present invention there is provided a process for the preparation of degradation products from proteinaceous material comprising the application of an enzyme material of the present invention to proteinaceous material.

According to a further aspect of the present invention there is provided a strain of *Micrococcus sedentarius* deposited under The Budapest Treaty at the National Collections of Industrial and Marine Bacteria on 24 May 1990 under the accession number NCIMB 40287.

DETAILED DESCRIPTION OF THE INVENTION

Figure 1:
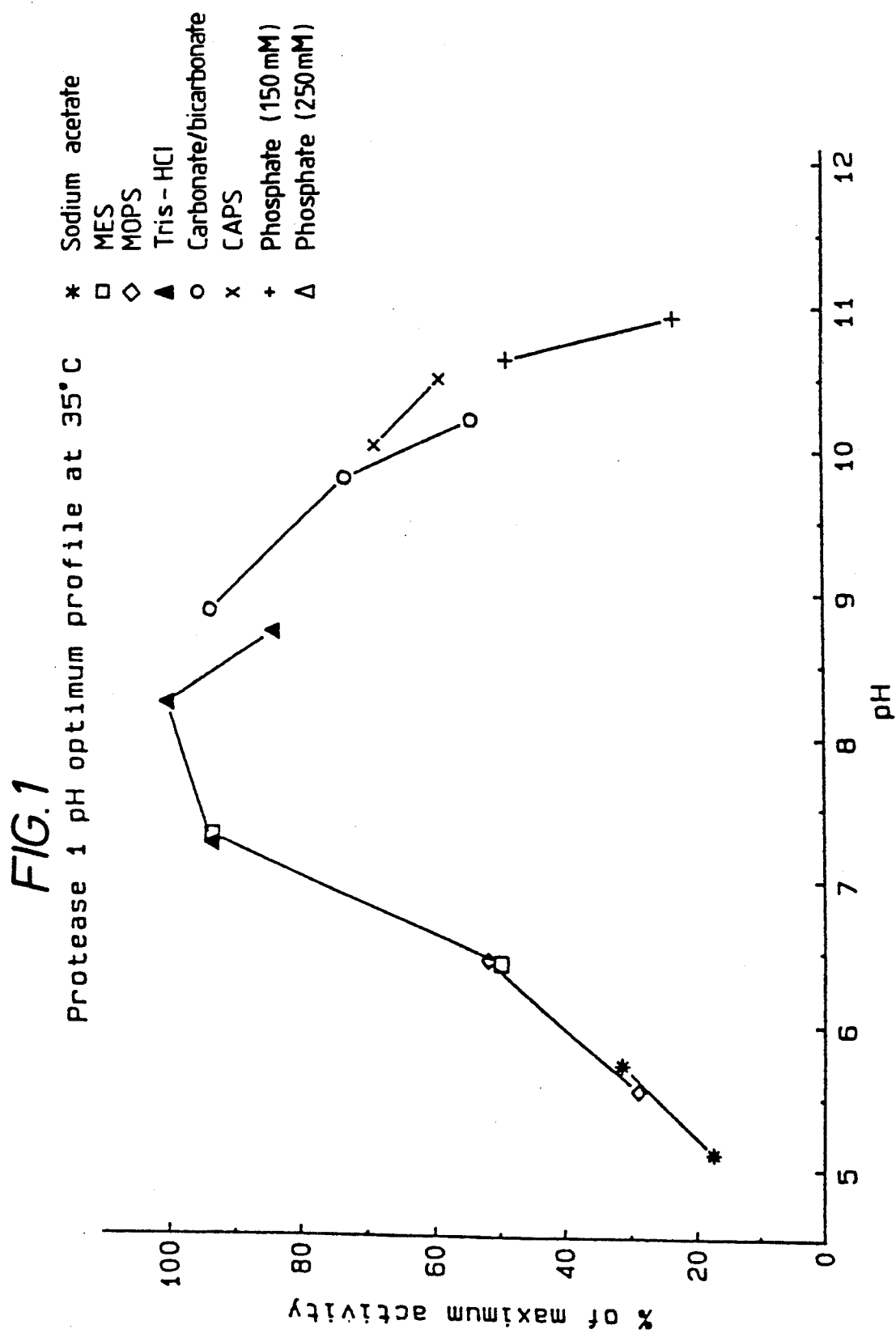
FIGS. 1 and 2 show the effect of pH on protease activity by Protease 1 and Protease 2 respectively.

Preferably, in a protein degradation or digestion process of the present invention, the pure enzyme material, a formulation thereof, or a cell-free culture of *Micrococcus sedentarius*, is applied to the material to be treated.

In one preferred embodiment the enzyme materials of the present invention are isolated from the strain *Micrococcus sedentarius* NCIMB 40287. *Micrococcus sedentarius* M17C was deposited with the International Depository Authority NCIMB Limited, 23 Street Machar Drive, Aberdeen AB2 1RY, on May 29, 1990 and has been designated NCIMB 40287. The above-referenced microorganism was deposited under the conditions of the Budapest Treaty on the international recognition of deposit of microorganisms for the purpose of patent procedure. All restrictions on the availability to the public of the material so deposited will be irrevocably removed upon the granting of a patent. Deposits will be maintained for a time period of 30 years from the date of the deposit or 5 years after the last request for the material, whichever is longer.

The enzyme materials of the second and third aspects of the present invention are hereinafter referred to as Protease 1 and Protease 2; these proteases having been obtained by culturing *Micrococcus sedentarius* NCIMB 40287.

Other strains of *Micrococcus sedentarius* will produce proteases which are similar to Protease 1 and 2, insofar as their biological activities are concerned. Such other proteases are intended to be within the scope of the invention. Various preferred features and embodiments of the invention will now be described by way of non-limiting example and with reference to the accompanying drawings in which:

The Micro-organism Micrococcus sedentarius NCIMB 40287

The micro-organism used for the production of Proteases 1 and 2 was isolated from the foot skin of an adult human. In particular, the strain *Micrococcus sedentarius* NCIMB 40287 was isolated from the foot skin of an adult human and was identified according to Kloos et al., Kloos, W. E., Tornabene, T. G. & Schliefer, K. H., International Journal of Systematic Bacteriology 24, 79–101, (1974) and Schleifer et al., Schleifer, K. H., Kloos, W. E. & Kocur, M., The genus *Micrococcus*. In The Prokaryotes, A Handbook on Habitats, Isolation and Identification of Bacteria, vol, 2. pp. 1539–1547, Edited by Starr. M. P., Stolp, H., Truper, H. G., Balows, A. and Schlegel, H. G. New York: Springer-Verlag. A culture of the organism has been deposited as indicated above. In addition to the specific micro-organism described and characterized herein, it should be understood that other strains of the micro-organism can also be cultivated to produce the product and all such strains are intended to be within the scope of the invention.

The following culture media may be used for growing the micro-organism: heated horse blood agar and, for fluid culture, a medium comprising 1% (w/v) Bacteriological Peptone, 1% (w/v) Yeast Extract and 0.5% (w/v) NaCl (BPYE). Storage may be effected either in 40% (v/v) glycerol-PBS (Phosphate Buffered Saline) at −20° C., or by freeze-drying. Colonies of *Micrococcus sedentarius* NCIMB 40287 appear wrinkled, buff and proteolytic on heated blood agar.

The following characteristics have been found:

| Microscopy tetrads. | Gram positive cocci in non-motile |
|---|---|
| Growth under anaerobic conditions | − |
| Catalase | + |
| Oxidase | − |
| Exopigment production | + brown |
| Growth on Simmons citrate agar | − |
| Growth on inorganic N agar | − |
| Growth on 7.5% NaCl agar | + |
| Nitrate reduction | − |
| Acetoin production | − |
| -galactosidase production | − |
| Acid from glucose | − |
| glycerol | − |
| mannose | − |
| Aesculin hydrolysis | − |
| Growth at 37° C. | + |
| Alginine hydrolysis | + |
| Casein hydrolysis | + |
| Production of methanethiol from methionine. | + |

| Antibiotic Sensitivities by the Disc Method. | | |
|---|---|---|
| Antibiotic | Disc amount | |
| Penicillin | 1 unit | R |
| Erythromycin | 10 μg | S |
| Chloramphenicol | 10 μg | S |

| | | |
|---|---|---|
| Kanamycin | 30 μg | S |
| Streptomycin | 10 μg | S |
| Novobiocin | 5 μg | S |
| Tetracycline | 10 μg | S |
| Neomycin | 30 μg | S |
| Vanomycin | 30 μg | S |
| Methicillin | 10 μg | R |

(R = resistant, S = sensitive)

Growth of Micrococcus sedentarius and Production of Proteases

The production of Proteases 1 and 2 may be effected by cultivating Micrococcus sedentarius. As previously mentioned Micrococcus sedentarius can be stored in glycerol-PBS or freeze-dried, and can be cultivated using BPYE. Crude supernatant fluid is then produced by centrifuging the culture. The supernatant fluid is then desalted and concentrated.

The following experimental results are provided for purposes of illustration and are not intended to limit the scope of the invention.

The following non-limiting examples further illustrate the preparation of Proteases 1 and 2.

EXAMPLE 1

Culturing

Freeze-dried cells on a paper strip were inoculated into 100 ml BPYE having the following composition:

| | |
|---|---|
| Bacteriological Peptone (Oxoid L37) | 1% (w/v) |
| Yeast Extract (Oxoid L21) | 1% (w/v) |
| NaCl (Sigma) | 0.5% (w/v) |

The culture was incubated at 37° C. for 48 hours with orbital shaking (160 rpm). Ten ml of this culture was used to inoculate BPYE+0.05% (v/v) polypropylene glycol 1025 (BDH). This medium was sterilized in 18 litre batches through a 0.2 μm porosity filter under nitrogen pressure into the nutrient reservoir of an LH Engineering 500 Series continuous culture apparatus. The apparatus had a culture working volume of 670 ml, with monitoring and control of pH, oxygen tension and temperature. The culture was stirred by direct drive at 900 rpm and maintained at pH 8.5±0.1, 35±0.2° C., and 74±4% oxygen tension with respect to air.

Two days after inoculation, the apparatus was switched to continuous mode and the dilution rate was set to 0.25 h$^{-1}$. After six culture volumes of medium had been used, a new harvest reservoir was connected, 7.3 litre culture was harvested at room temperature and NaN$_3$ was added to 0.05% (w/v).

EXAMPLE 2

Production of Crude Supernatant Fluid

Cells were removed from cultures by centrifugation in 250 ml volumes at 5000 g for 10 minutes at 4° C. The supernatant fluids were pooled, pumped into plastic blood-storage bags and stored at −30° C.

EXAMPLE 3

Desalting and Concentration of the Proteases

The supernatant fluid was desalted and concentrated using a 90 mm PM10 ultrafiltration membrane (10,000 molecular weight cut-off, Amicon) held in an Amicon TCF 10A pumped-flow cell at 4° C. The ultrafiltration was undertaken using 30 psi (206,820 Pa) oxygen-free nitrogen. When the volume above the membrane was 220 ml, 220 ml 0.05% (w/v) NaN$_3$ was added and again the volume reduced to 220 ml. Further desalting was carried out using continuous flow of 4 litre 0.05% (w/v) NaN$_3$. The volume of retentate was reduced to 183 ml and 20 ml aliquots were stored at −30° C.

Purification of Proteases 1 and 2

Resolution and purification of the proteases from 15 ml of retentate is effected by column chromatography firstly by ion-exchange, secondly by hydrophobic interaction and finally by affinity. Protease-containing fractions from each chromatographic procedure were stored at −30° C. until required.

The following non-limiting examples further illustrates purification:

EXAMPLE 4

Ion-exchange Chromatography

Fifteen ml retentate was mixed with 3.75 ml 50 mM Tris-HCl, 0.25% (w/v) NaN$_3$ pH 8.0 buffer and applied to a DEAE-Sepharose Fast-Flow anion-exchange column (column dimensions 2.2×50 cm, bed volume 36 ml), pre-equilibrated with starting buffer (10 mM Tris-HCl, 0.5% (w/v) NaN$_3$ pH 8.0), at a flow rate of 60 ml h$^{-1}$ (linear flow rate 15.8 cm h$^{-1}$) at 4° C. After loading, the column was flushed with 20 bed volumes of starting buffer, to elute unbound substances, and 12 ml fractions were collected. No proteolytic activity was detected in these fractions.

Bound substances were then eluted using a 1.6 liter linear gradient of increasing ionic strength, from 0–0.5M NaCl in starting buffer. Fractions (8 ml) were collected and Protease 1 eluted between 70 and 440 ml after the start of the NaCl gradient. Maximum Protease 1 eluted in eight fractions (112–176 ml after the start of the gradient) corresponding to 0.03–0.05M NaCl. A single protein band of 30.3 kDa was observed when 4 μl of each of the eight fractions were analyzed by SDS-PAGE and silver staining. Protease 2 eluted between 720 and 912 ml after the start of the NaCl gradient with maximum Protease 2 activity eluting in 13 fractions (736–840 ml after the start of the gradient) corresponding to 0.23–0.25 M NaCl. Four μl of each of the 13 fractions showed multiple polypeptide bands, with a major band at 50 kDa, when analyzed by SDS-PAGE and silver staining. There was a great reduction in the number of polypeptide species compared to that in the retentate. Equal volumes of the 13 fractions were pooled (total volume 92 ml), concentrated 10.3-fold and desalted by 85% using a PM10 ultrafiltration membrane (molecular weight cut-off 10,000; Amicon) using oxygen-free nitrogen at 30 psi, at 4° C., resulting in 8.8 ml semi-pure Protease 2.

EXAMPLE 5

Hydrophobic Interaction Chromatography

Two ml of semi-pure Protease 2 was applied to a Phenyl-Sepharose CL-4B hydrophobic interaction column (column dimensions 2×15 cm, bed volume 13.7 ml), pre-equilibrated with 1.5M (NH$_4$)$_2$SO$_4$ in starting buffer (10 mM Tris-HCl, 0.05% (w/v) NaN$_3$ pH 8.0), at a flow rate of 12 ml h$^{-1}$ (linear flow rate 6 cm h$^{-1}$) at 4° C. After loading, the column was flushed with five bed volumes of starting buffer, to elute unbound substances, and 4 ml fractions were collected. No proteolytic activity was detected in these fractions. Bound substances were then eluted using a 274 ml linear gradient of decreasing $(NH_4)_2SO_4$ concentration, from 1.5–0M $(NH_4)_2SO_4$ in starting buffer, and 4 ml fractions were collected. Protease 2 eluted in seven fractions (232–260 ml after the start of the gradient) with maximum Protease 2 eluting between 244 and 256 ml after the start of the gradient, corresponding to about 0.1M $(NH_4)_2SO_4$. A major polypeptide band of 50 kDa was observed when 4 μl volumes of each of the seven fractions were analyzed by SDS-PAGE and silver staining. A minor polypeptide band was a slightly higher molecular weight was also observed. Volumes (0.3 ml) of each of the seven fractions were pooled and concentrated to 82 μl using a Centricon 10 Microconcentrator with a 10,000 molecular weight cut-off (Amicon).

EXAMPLE 6

Affinity Chromatography

Fifty μl of the concentrated fractions from the hydrophobic interaction column was mixed with 250 μl 5 mM Tris-HCl, 0.5% $NaN_3$ pH 8.0 buffer, and loaded onto a Benzamidine-Sepharose 6B affinity column (column dimensions 1×15 cm, bed volume 5.8 ml), pre-equilibrated with 5 mM Tris-HCl, 0.05% $NaN_3$ pH 8.0 starting buffer, at a flow rate of 6 ml $h^{-1}$ (linear flow rate 7.5 cm $h^{-1}$) at 4° C. After loading, the sample was allowed to absorb without buffer flow for 30 minutes and then the column was flushed with 6.7 bed volumes of starting buffer, to elute unbound substances, and fractions (1.5 ml) were collected. No proteolytic activity was detected in these fractions. Bound substances were then eluted using a 29 ml linear gradient of increasing ionic strength, from 0–0.2M NaCl in 75 mM Tris-HCl, 0.05% (w/v) $NaN_3$ pH 8.0 buffer, and fractions (1.5 ml) were collected.

Protease 2 eluted in four fractions (22.5–28.5 ml after the start of the gradient) corresponding to about 0.18M NaCl. A single polypeptide band, with a molecular weight of 50 kDa was observed when 4 μl of each of the four fractions were analyzed by SDS-PAGE and silver staining. The four fractions containing Protease 2 were stored at −30° C.

Properties of Protease 1 and Protease 2

The following methodology was used to determine the activities of the proteases of this invention:

Detection of Proteolytic Activity

Proteolytic activity was determined in fractions eluted from chromatography columns or in samples applied to isoelectric focusing (IEF) analytical gels using casein as a substrate. For the detection of proteolytic activity in column fractions, the following procedure was used. Hammarsten casein was dissolved, at a concentration of 0.6% (w/v), in 015M sodium carbonate/sodium hydrogen carbonate buffer (pH 10.0) by boiling for 2 minutes. Ten ml of the casein solution (at 60° C.) was added to an equal volume of molten (60° C.) 2% (w/v) agarose in the same buffer and poured into the lid of a 8.4×12.7 cm microtitre plate and allowed to set. Wells (2.5 mm diameter) were punched in the agarose and 5 μl of each test fluid (column fraction) was pipetted into the wells. The plates were placed in a moist chamber and incubated at 37° C. After overnight incubation, proteolytic activity was visualized by precipitation of casein in the gel by flooding the plate with 10% (w/v) trichloroacetic acid (TCA). Proteolytic activity was indicated by a zone of clearing around a well against a white background of precipated casein.

Agarose-casein gels containing buffer at pH 10.0 were used for the detection of proteases in IEF gels. Agarose-casein gels were prepared as described above for the detection of proteolytic activity in column fractions. The position of a protease in a IEF gel was determined by carefully laying the loaded and electrofocused IEF gel onto the surface of a casein-agarose gel. After overnight incubation at 37° C., the position of the IEF gel was marked and the IEF gel removed. The casein-agarose plate was flooded with 10% (w/v) TCA and the position of the protease observed as a band of clearing.

Quantitative Method

Additional methods were used for the quantitative assay of protease activity. These methods are hereinafter referred to as the "Quantitative Method."

Quantitative Method—Protease 1

A reaction mixture comprising 1 ml enzyme solution and 1 ml 4% (w/v) azo-casein in 150 mM Tris-HCl buffer (pH 8.5 at room temperature or pH 8.1 at 40° C.) was incubated at 40° for 30 minutes, 2 ml of trichloroacetic acid (TCA) (10%, w/v) was added to the reaction mixture at time zero and to a duplicate tube after incubation. TCA-precipitated material was removed by filtration through Whatman No. 1 filter paper. 1.5 ml filtrate was added to 0.225 ml NaOH (10M) and the absorbance was determined spectrophotometrically at 440 nm. Enzyme blanks were included and assays were performed in duplicate.

Quantitative Method—Protease 2

Protease 2 was assayed as described for Protease 1, except 250 mM sodium phosphate buffer (pH 10.75 at room temperature or pH 10.1 at 45° C.) was used and the reaction mixture was incubated at 45° C. for 9 minutes. The pHs of the buffers for these assays were adjusted at room temperature.

With the exception of the determination of the optima pH and range of activity of Protease 1 and Protease 2 which used the assay method described on hereinafter, the quantitative methods described above were used subsequently for determination of Protease 1 and Protease 2 activities.

Volumes of enzyme-containing solutions (referred to as "fraction" in Table 1) were assayed for protease activity by the quantitative method and for protein using BCA Protein Assay Reagent (Pierce Chemical Co., Chester, England) according to the manufacturer's instructions.

The quantitative method (protease activity) for Protease 2 was used to assay all fractions except "Ion Exchanged P1" which was assayed using that described for Protease 1. The results are shown in Table 1. Protease 1 was purified from 7.3 liters of crude culture supernatant fluid with a purification factor and yield of 2.2-fold and 0.3% respectively. Protease 2 was purified from crude supernatant fluid with a purification factor and yield of 28.9-fold and 38.5% respectively. In Table 1 the purification factor is shown with respect to total protease activity in the crude supernatant fluid.

TABLE 1

| | Purification of Micrococcus sedentarius Protease 1 and Protease 2. | | | | | | | |
|---|---|---|---|---|---|---|---|---|
| Fraction | Volume (ml) | Protein Conc. (mg ml$^{-1}$) | Total Protein (mg) | Activity (U ml$^{-1}$) | Total Activity (U) | Specific Activity (U mg$^{-1}$) | Yield % | Purification Factor |
| Crude Supernatant | 7,300 | 4.38 | 32,003 | 265 | $1.94 \times 10^6$ | 60.5 | 100.0 | — |
| Fluid Crude Amicon Retentate | 183 | 7.95 | 1,456 | 8,020 | $1.26 \times 10^6$ | 1008 | 75.8 | 16.7 |
| Ion Exchanged P1 | 842 | 0.05 | 39 | 6 | $5.24 \times 10^3$ | 135 | 0.3 | 2.2 |
| Ion Exchanged P2 | 1,110 | 0.51 | 562 | 1,008 | $1.12 \times 10^6$ | 1,991 | 57.8 | 32.9 |
| Concentrated IEX P2 | 107 | 4.94 | 530 | 9,825 | $1.02 \times 10^6$ | 1,988 | 54.5 | 32.8 |
| HIC | 1,502 | 0.28 | 416 | 605 | $9.09 \times 10^5$ | 2,184 | 47.0 | 36.1 |
| Desalted HIC | 1,502 | 0.26 | 391 | 643 | $9.66 \times 10^5$ | 2,473 | 50.5 | 40.9 |
| Affinity | 7,041 | 0.06 | 425 | 106 | $7.42 \times 10^5$ | 1,749 | 38.5 | 28.9 |

Detection of Callus-Degrading Activity

A suspension of foot callus skin was prepared as follows and referred to as finely ground callus.

The foot callus was finely chopped in a glass Petri dish with a scalpel, ground in liquid nitrogen with a mortar and pestle, sieved through a wire gauze (1 mm mesh size), homogenized in water using a Griffin homogenizer (TKW-300-050N, Gallenkamp), and centrifuged at 5000 g for 15 minutes.

The resulting pellet was freeze-dried, ground with a mortar and pestle, and the resulting finely ground callus was stored at $-30°$ C.

Callus-degrading activity was determined in fluid samples and in samples applied to an IEF analytical gel using the foot skin callus (described above) as a substrate. Callus-agarose was prepared as follows. A suspension of finely ground callus with an optical density at 700 nm of 0.6–0.7 was prepared in 0.2M sodium phosphate buffer (pH 7.6). Ten ml of this suspension was heated to 60° C., mixed with an equal volume of molten (60° C.) 2% (w/v) agarose in the same buffer, poured into the lid of a $8.4 \times 12.7$ cm microtitre plate and allowed to set. Wells (2.5 mm diameter) were punched in the agarose and 5 µl of each test fluid was pipetted into the wells. The plates were incubated as for the proteolytic activity test. After incubation, callus-degrading activity was indicated by a zone of clearing, best observed using a light-box with a dark background.

The position of a protein, which caused callus degradation on an IEF gel, was determined in a similar manner as that for proteolytic activity except that the casein-agarose gel was replaced by a callus-agarose gel and the plate was not flooded with TCA.

Quantitative Method

Additional methods were also used for the quantitative assay of callus-degrading activity. Callus-degrading activity was assayed as follows (specific details are described later in the text where appropriate). A suspension of the finely ground callus (described above) with an optical density at 700 nm ($OD_{700}$) of 0.6–0.7 was prepared in a buffer containing 0.02% (w/v) sodium azide. 1 ml enzyme solution was added to 2 ml pre-warmed callus suspension (at the required temperature) in a spectrophotometer cuvette. The $OD_{700}$ was recorded immediately and after 1 h incubation at the required temperature with stirring.

1 unit (U) of callus-degrading activity is defined as that which causes a reduction in $OD_{700}$ of 0.001 in 1 h. The method is also disclosed in an article by K. T. Holland et al., Qualitative and Quantitative assay for detection of callus-degrading activity by bacteria. Letters in Applied Microbiology 11, 224,227.

Isoelectric Point (pI) of Protease 1 and Protease 2

The isoelectric point (pI) of Proteases 1 & 2 may be determined as follows: Polyacrylamide IEF gels were prepared according to Winter et al. (5) except that 10 µl N-N-N-N-tetramethylethylenediamine was added to the degassed gel solution prior to pouring into the mould, and the carrier ampholyte mixture contained 2.76 ml Pharmalyte 2.5–5.0 and 0.24 ml Ampholine 5.0–8.0, Pharmalyte and Ampholine are commercially available from Pharmacia. The electrode solutions were 0.1M phosphoric acid (anode) and 0.1M sodium hydroxide (cathode).

Samples (20 µl) were applied using paper applicators and gels were run at 9 W constant power for 3 h. The gel was loaded with three sets of samples. After electrophoresis, the gel was cut into three equal sections so that each contained a full set of samples. One section was placed onto a casein-agarose gel for detection of proteolytic activity, one onto a callus-agarose gel for detection of callus-degrading activity, and the remaining section was fixed and stained for the detection of protein, as described in Winter et al., Analytical Electrofocusing in Thin Layers of Polyacrylamide Gels, LKB Application Note 250, (1977).

The position of each protease was determined by measuring the distance between the center of a zone of clearing on the casein-agarose plate and the position of the anode. The pI of each protease was then determined using a calibration curve of gel pH (measured using a surface pH electrode) plotted against distance from the anode.

The pI of Protease 1 was 4.6 and the pI of Protease 2 was 2.7. Protease 1 and Protease 2 were both proteolytic and degraded callus.

Molecular Weights of Protease 1 and Protease 2

The molecular weights of Protease 1 and Protease 2 may be determined as follows: The denatured, reduced polypeptide molecular weights of Protease 1 and 2 were determined by SDS-PAGE according to the method of Laemmli, Cleavage of structural proteins during the assembly of the head of bacteriophage T4. Nature 227, 680–685, (1970). Samples (10 µl) were boiled for 2 minutes with 10 µl sample buffer containing 6% (w/v) SDS and 10% (v/v) mercaptoethanol. Eight µl of the boiled sample was loaded onto a 12% (w/v) polyacrylamide gel ($0.075 \times 5.5 \times 8$ cm) in a LKB Midget electrophoresis system and electrophoresed at 30 mA for 30 minutes.

The gel was fixed and silver stained with Gelcode (Pierce), according to the manufacturer's instructions.

The molecular weight of each protease was determined using a calibration curve of polypeptide position plotted against the molecular weight of known standard polypeptides.

The estimated molecular weights of Proteases 1 and 2 were 30.3 and 50.0 kDa, respectively.

The pH Optima and Ranges of Activity of Protease 1 and Protease 2

Figure 2:
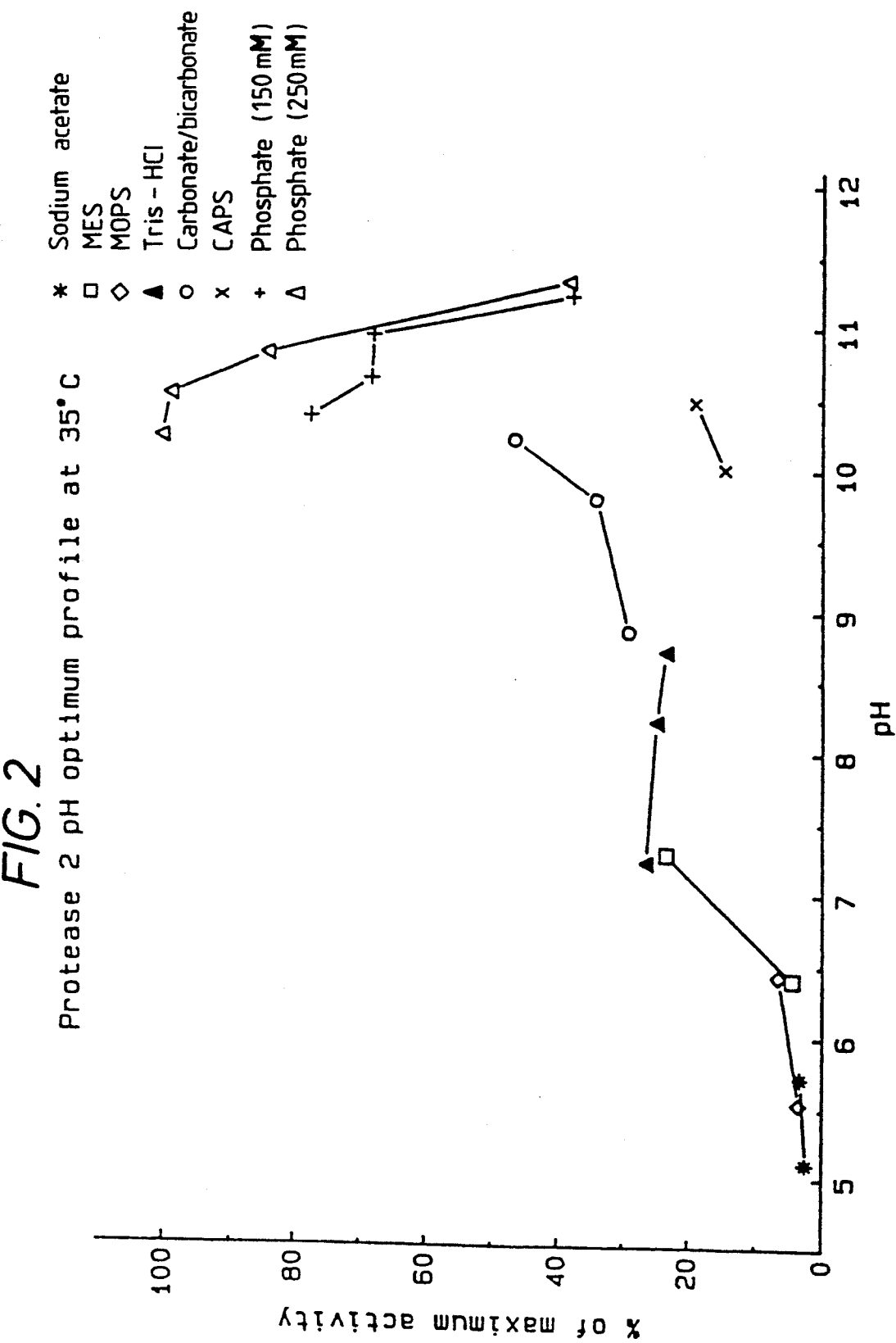

The pH optima and ranges of activity of Protease 1 and Protease 2 may be determined as follows, and with reference to the accompanying drawings, in which FIG. 1 shows the effect of pH on the activity of Protease 1, and FIG. 2 shows the effect of pH on the activity of Protease 2.

Preliminary experiments using supernatant fluids from *Micrococcus sedentarius* cultures with mixtures of Protease 1 and Protease 2 in unknown ratios were carried out which had shown that maximum proteolytic activity was obtained at pH 10.0 in 015M sodium carbonate/sodium hydrogen carbonate buffer. The purified Proteases 1 and 2 were tested for activity in a range of 015M buffers at pH values from 5.1 to 11.4 using the protease assay described by Millet, Characterization of proteinase excreted by *Bacillus subtilis* Marburg strain during sporulation. Journal of Applied Bacteriology 33, 207–219, (1970). The reaction mixture, comprising 1 ml enzyme solution and 4 ml of 2% (w/v) azocasein in buffer, was incubated at 35° C. for 2 h. The pH of each reaction mixture was determined after 2 h incubation at 35° C. At time zero and after 2 h incubation, 2 ml reaction mixture was added to 2 ml TCA (10%, w/v). After filtration through Whatman No. 1 filter paper, the concentration of TCA-soluble azo-peptides released by proteolytic activity was determined spectrophotometrically at 440 nm. Enzyme blanks were included. One unit of enzyme activity was defined as the amount which produced an increase in absorbance at 440 nm of 0.001 in 1 h at 35° C. More generally, one unit of enzyme activity is defined as the amount which produces an increase in absorbance at 440 nm of 0.001 at 1 h (at the assay temperature). The results are shown in FIGS. 1 and 2. Proteases 1 and 2 were detected in the range 5.1–10.9 and 5.1–11.3 respectively. Maximum activity was detected at pH 8.2 in 0.15M Tris-HCl buffer for Protease 1 and at pH 10.2 in 0.25M phosphate buffer for Protease 2.

Protease Activity—Optimum temperature

The optimum temperatures for assaying Proteases 1 and 2 were determined. The quantitative assay method was used for assaying protease activity, with the modifications described below.

Protease 1 was assayed in 250 mM sodium phosphate buffer with pHs as follows:

| pH | Temperature |
|---|---|
| 8.5 | Room Temp. |
| 8.2 | 35° C. |
| 8.1 | 40° C. |

1.36 Protease Units were incubated in the assay system for 27 minutes at various temperatures. Protease 1 activity was detected from 20° to 60° C. with the optimum temperature at 40° C.

Protease 2 was assayed in 150 mM Tris-HCl with pHs as follows:

| pH | Temperature |
|---|---|
| 10.75 | Room Temp. |
| 10.2 | 35° C. |
| 9.9 | 46° C. |

Figure 3:
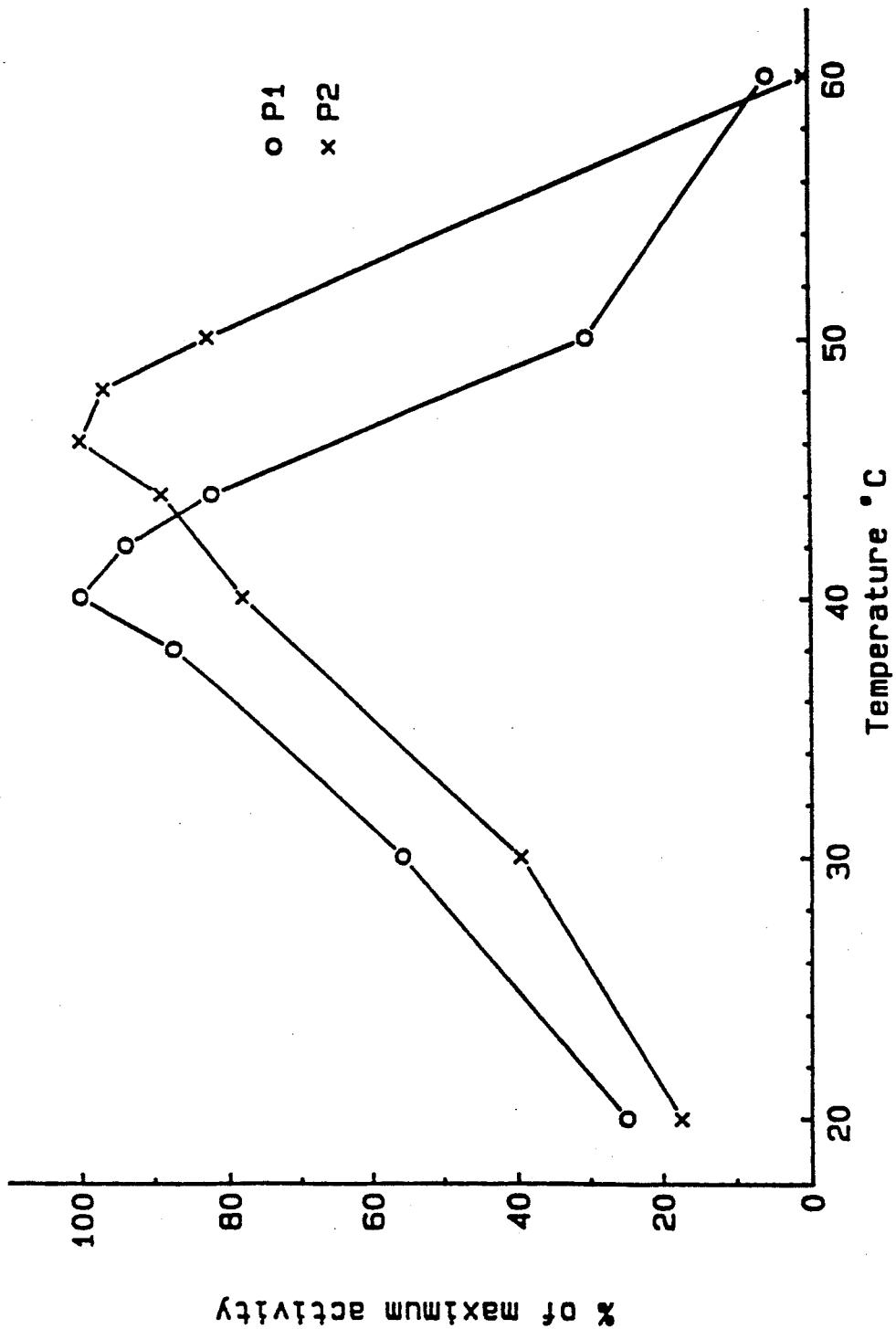
FIG. 3 shows temperature optimum curves for Proteases 1 and 2.

4.1 Protease Units were incubated in the assay system for 9 minutes at various temperatures. Protease 2 activity was detected from 20° to 50° C. with the optimum temperature at 46° C. The results are illustrated in FIG. 3.

Callus-Degrading Activity—Optimum Temperature

Preliminary experiments showed that Proteases 1 and 2 had highest callus-degrading activity at a pH of approximately 7.6. Therefore, the optimum temperatures for assaying callus-degrading activity of Protease 1 and Protease 2 were determined at pH 7.6 using the quantitative assay.

Figure 4:
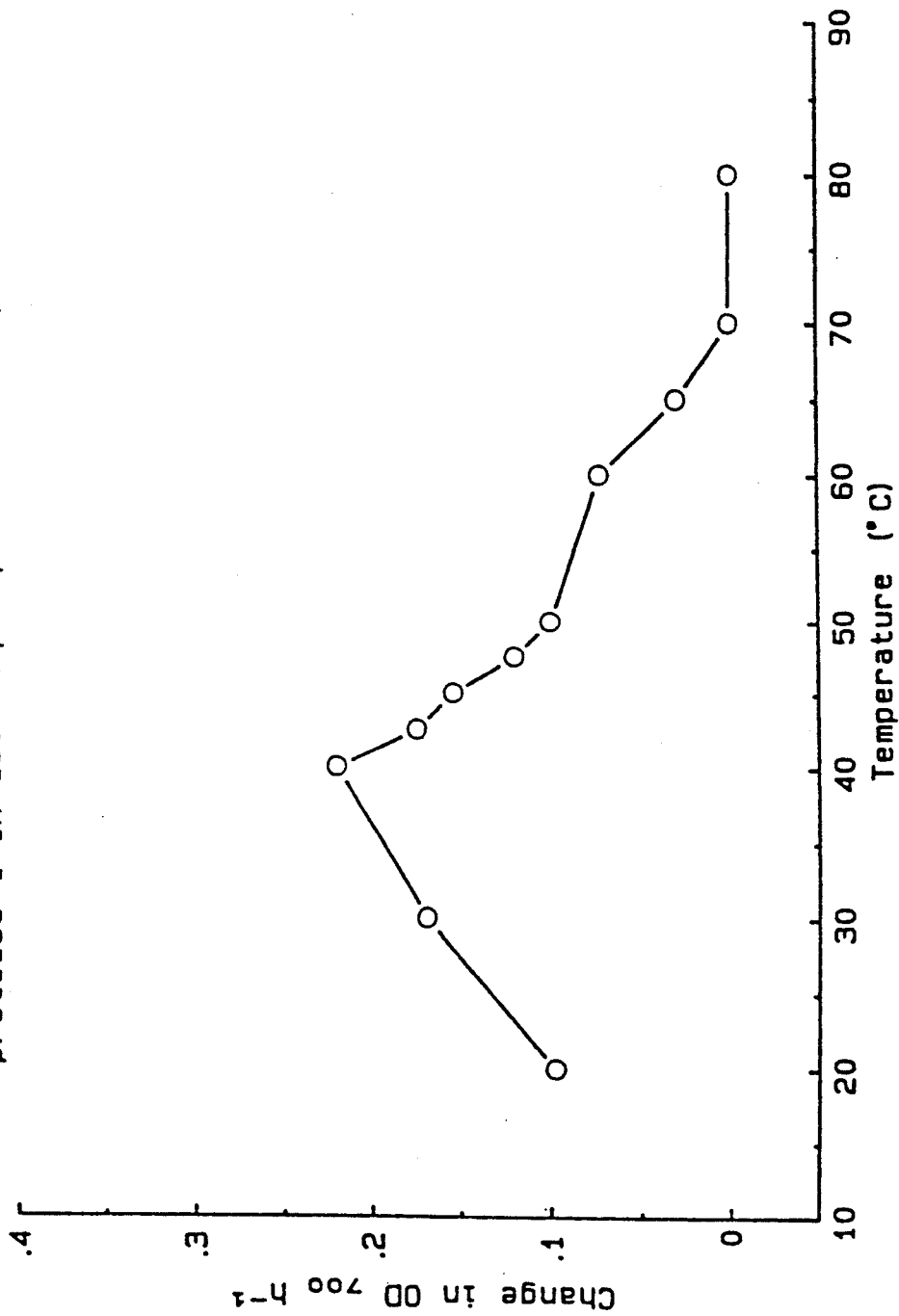
FIGS. 4 and 5 show the effect of temperature on callus degradation by Protease 1 and Protease 2 respectively.

Protease 1 (3 Protease Units) was incubated in 150 mM sodium phosphate buffer (pH 7.6) at various temperatures. Callus-degrading activity was detected from 20° to 65° C. with the optimum at 40° C. The results are shown in FIG. 4.

Figure 5:
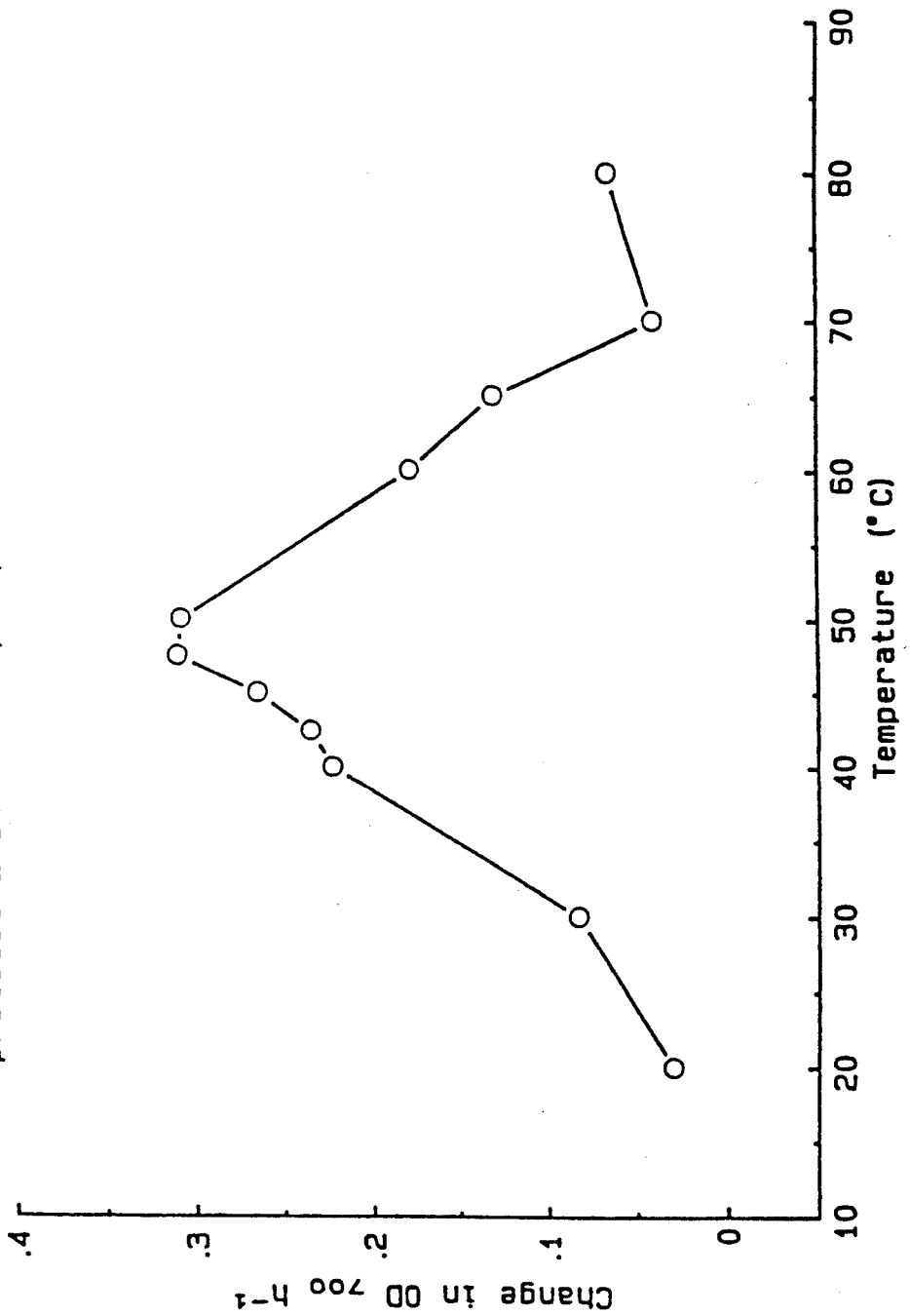

Protease 2 (3 Protease units) was incubated in 150 mM sodium phosphate buffer (pH 7.6) at various temperatures. Callus-degrading activity was detected from 20° to 80° C. with the optimum at 50° C. The results are shown in FIG. 5.

Callus-Degrading Activity—Optimum pH

Figure 6:
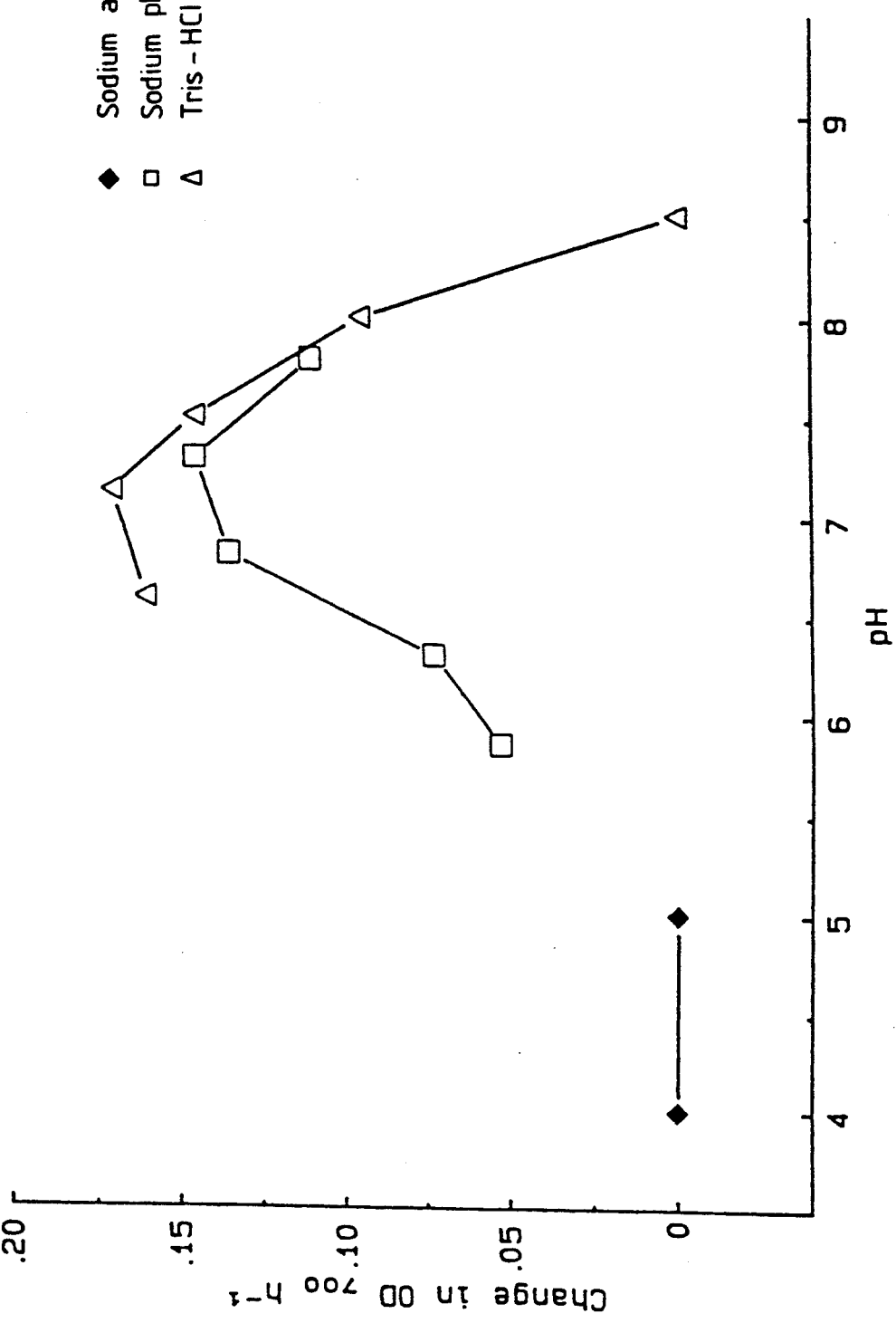
FIGS. 6 and 7 show the effect of pH on callus degradation by Protease 1 and Protease 2 respectively.
Figure 7:
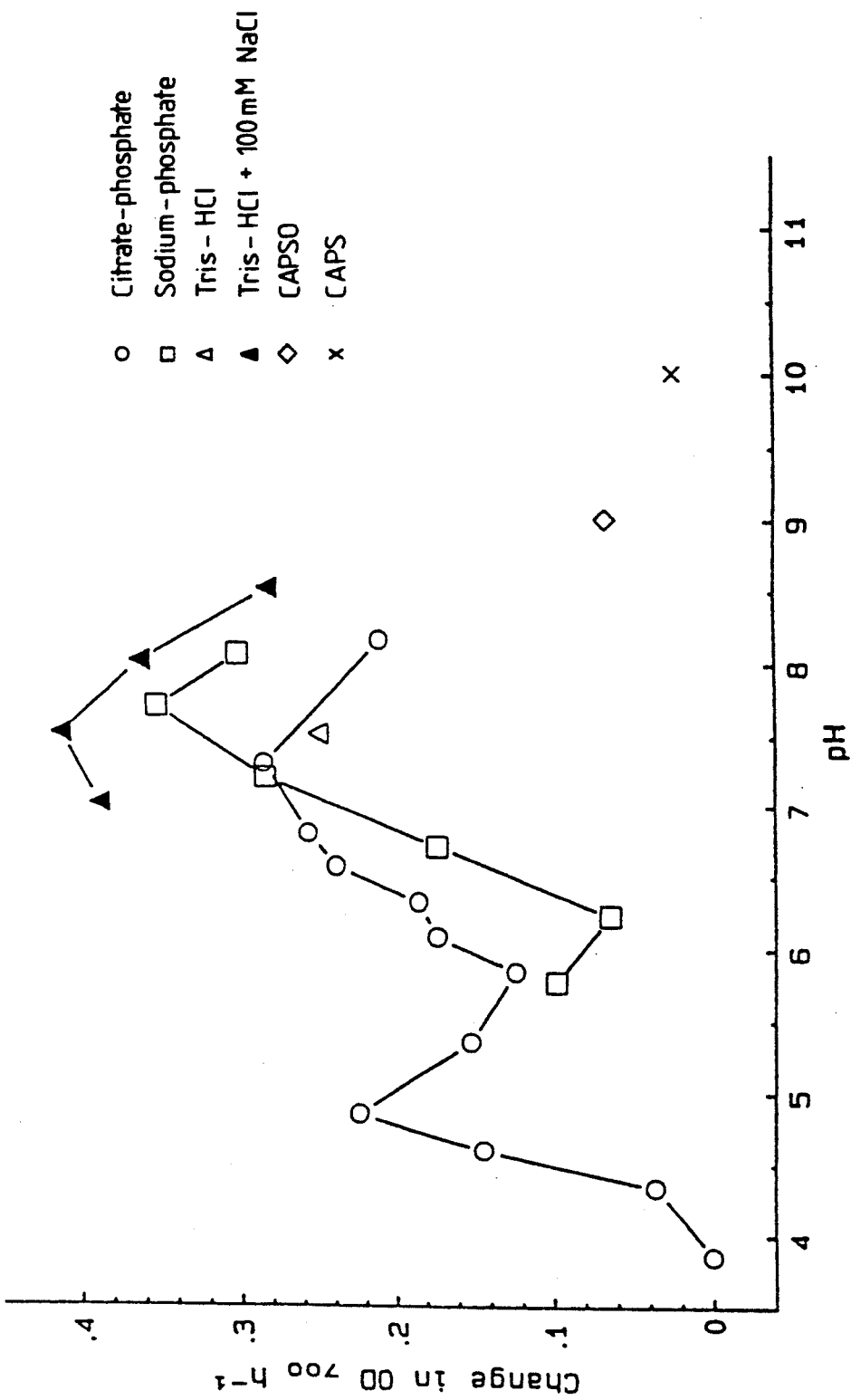

The optimum pH for activity of Proteases 1 and 2 were determined at their optimum temperatures. The quantitative assay was used with 150 mM buffers, as indicated in FIGS. 6 and 7.

Protease 1 (4.5 Protease Units) was assayed at 40° C. Callus-degrading activity was detected from pH 5.9 to 8.0 with the optimum at pH 7.1 in Tris-HCl buffer. The results are shown in FIG. 6.

Protease 2 (59 Protease Units) was assayed at 50° C. Callus-degrading activity was detected from pH 4.3 to i0.0 with two peaks of activity at pH 4.9 and 7.5. The optimum activity was detected at 7.5 in Tris-HCl buffer containing 100 mM NaCl. The results are shown in FIG. 7.

All pH measurements for callus-degrading activity were determined at the temperature of the assay.

Further Characterization of Proteases 1 and 2

The Effect of Cysteine of Protease Activity

Protease 1 was incubated at a concentration of 1.2 Protease Units ml$^{-1}$ at 4° C. for 1 h, in the presence and absence of 100 mM cysteine, in 150 mM Tris-HCl buffer (pH 8.5). The activity of Protease 1 after incubation with 100 mM cysteine was 106% that in the absence of cysteine.

Protease 2 was incubated at a concentration of 3.0 Protease Units ml$^{-1}$ at 4° C. for 1 h, in the presence and absence of 100 mM cysteine, in 250 mM sodium phosphate buffer (pH 10.75). The activity of Protease 2 after incubation with 100 mM cysteine was 105% that in the absence of cysteine.

The Effect of EDTA on Protease Activity

Protease 1 was incubated at a concentration of 0.75 Protease Units ml$^{-1}$ at 4° C. for 1 h, in the presence and absence of 10 mM EDTA, in 150 mM Tris-HCl buffer (pH 8.5). The activity of Protease 1 after incubation with 10 mM EDTA was 34% that in the absence of EDTA.

Protease 2 was incubated at a concentration of 3.0 Protease Units $ml^{-1}$ at 4° C. for 1 h, in the presence and absence of 10 mM EDTA, in 250 mM sodium phosphate buffer (pH 10.75). The activity of Protease 2 after incubation with 10 mM EDTA was 17% that after incubation in the absence of EDTA.

The Effect of PMSF on Protease Activity

Protease 1 was incubated at a concentration of 1.2 Protease Units $ml^{-1}$ at 4° C. for 1 h, in the presence and absence of 5 mM PMSF (phenylmethyl sulfonyl fluoride) in 150 mM Tris-HCl buffer (pH 8.5). The activity of Protease 1 after incubation in the presence of 5 mM PMSF was 0% that in the absence of PMSF.

Protease 2 was incubated at a concentration of 3.1. Protease Units $ml^{-1}$ at 4° C. for 1 h, in the presence and absence of 5 mM PMSF, in 250 mM sodium phosphate buffer (pH 10.75). The activity of Protease 2 after incubation in the presence of 5 mM PMSF was 58% that in the absence of PMSF.

Activity and Stability of Proteases 1 and 2 in the Presence of $CaCl_2$

Activity

Protease 1 was incubated at a concentration of 1.2 Protease Units $ml^{-1}$ in 150 mM Tris-HCl buffer (pH 8.5) containing 0 and 10 mM $CaCl_2$. The effect of $CaCl_2$ on the activity of Protease 1 was determined by assaying protease activity immediately following the addition of $CaCl_2$ (t=0). The activity of Protease 1 in the presence of $CaCl_2$ was 129% that in the absence of $CaCl_2$.

Stability

To investigate the effect of $CaCl_2$ on the stability of Protease 1 protease activity was assayed after 1 h incubation at 37° C. with 10 mM $CaCl_2$. The activity of Protease 1 after incubation in the presence of $CaCl_2$ was 114% that at t=0 whereas after incubation in the absence of $CaCl_2$, the activity was 19% that at t=0.10 mM $CaCl_2$, therefore, increased the activity and stability of Protease 1 at 37° C.

Protease 2

Due to the increased stability of Protease 2, it was necessary to incubate the enzyme at 60° C. to determine whether it would be stabilized by 10 mM $CaCl_2$. Protease 2 was incubated at a concentration of 63 Protease Units $ml^{-1}$ in buffers, at various pH values, containing 0 and 10 mM $CaCl_2$ for up to 4 h. The buffers were as follows and the pHs were measured at room temperature:

| pH | Buffer (30 mM) |
|---|---|
| 5 | Sodium acetate |
| 6 | MES |
| 7-9 | Tris-HCl |

Figure 8:
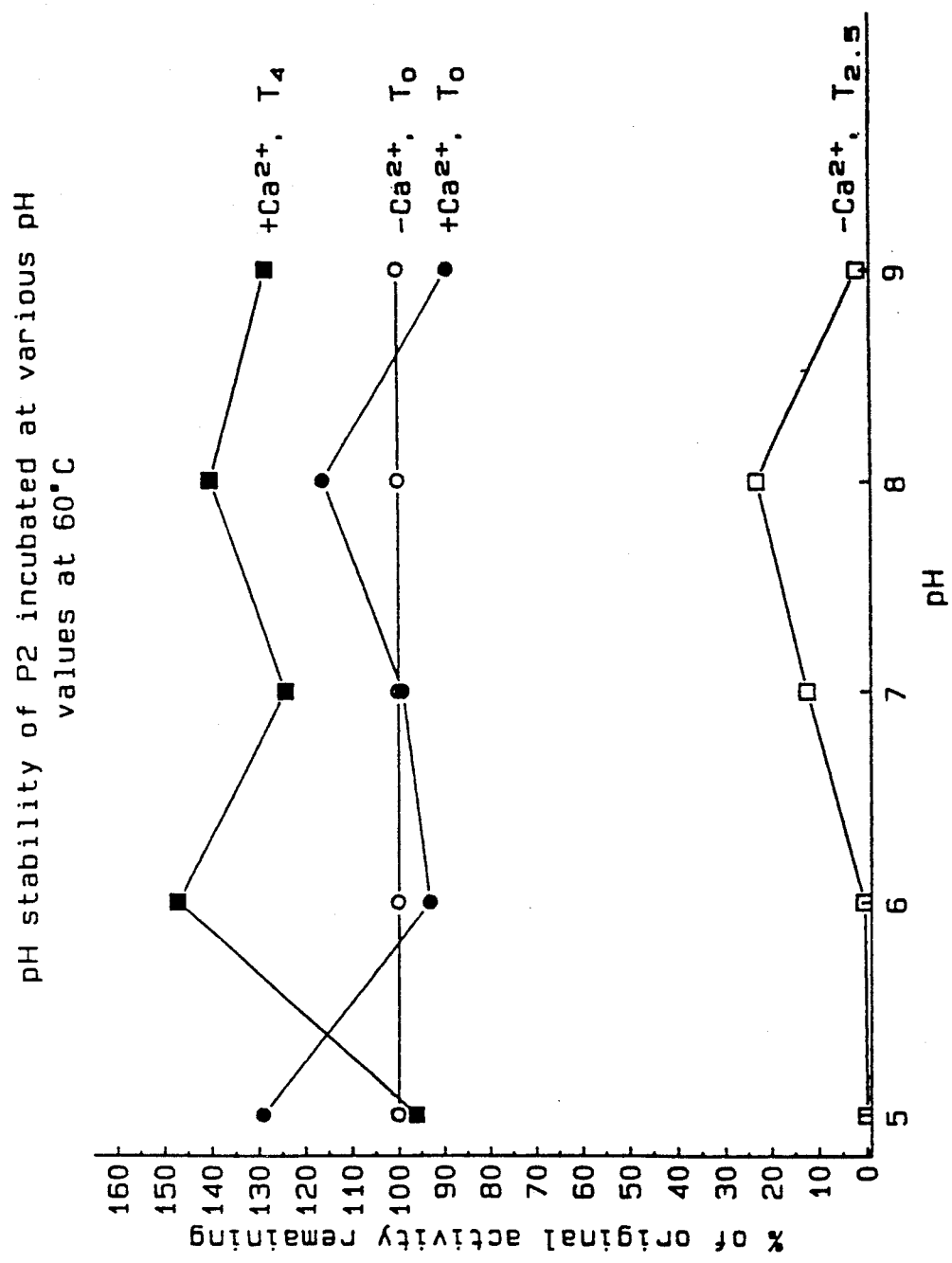
FIG. 8 shows the effect of calcium chloride on the stability of Protease 2.

Protease activity was determined immediately following addition of 10 mM $CaCl_2$ (t=0) and at various times thereafter. The results are shown in FIG. 8.

The presence of 1 mM $CaCl_2$ in the protease assay did not stimulate Protease 2 activity at pH 6 or 7 at t=0. Activity was stimulated by 1 mM $CaCl_2$ at pH 5 and 8, and slightly inhibited at pH 9 at t=0. In the absence of $CaCl_2$, Protease 2 appeared to have greatest stability at pH 8 (28% that at t=0). In the presence of $CaCl_2$, Protease 2 was stable at all pH values tested (5-9) and activity apparently increased between pH 6 and 9.

Stability of Proteases 1 and 2 at Various Temperatures

Proteases 1 and 2 were incubated in 30 mM buffers at various pHs and assayed for Protease activity at time intervals. The buffers were as follows, at room temperature:

| pH | Buffer |
|---|---|
| 5.0 | Sodium acetate |
| 5.9 | MES |
| 6.9-8.7 | Tris-HCl |
| 9.8 | Carbonate bicarbonate |
| 10.7 | Sodium phosphate |

All buffers contained 0.05% (w/v) sodium azide. Protease 1 was incubated at a concentration of 1.0 Protease Units $ml^{-1}$ and Protease 2 at 15.8 Protease Units $ml^{-1}$ in the storage buffers.

Stability at 4° C.

Figure 9:
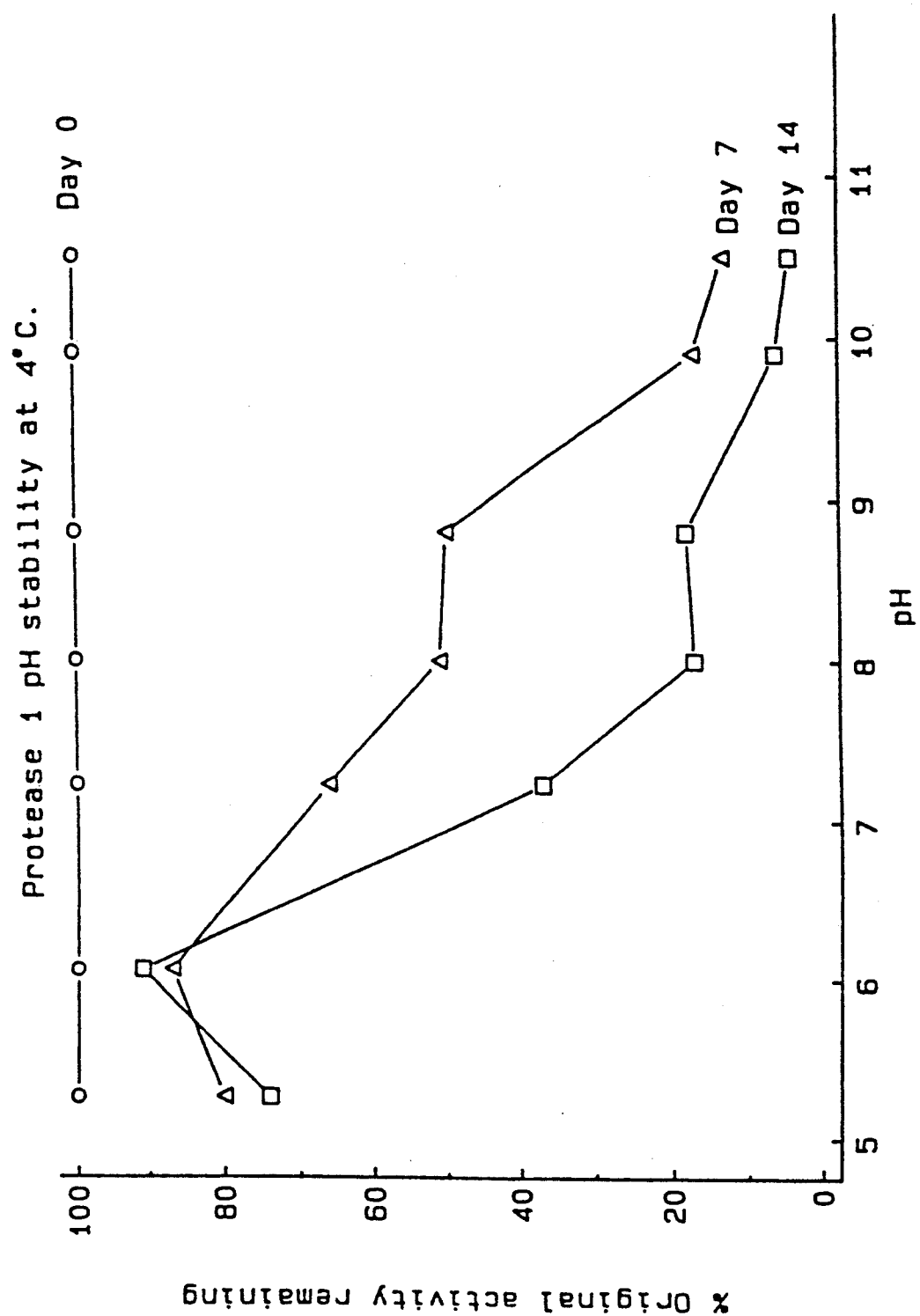
FIGS. 9 and 10 show the pH stability of Protease 1 and Protease 2 respectively at 4° C.

Protease 1 The results are shown in FIG. 9. The stability of Protease 1 was greatly affected by pH. Approximately 80% of the original activity remained after 14 days at pH 5 and 6. At higher pHs, stability decreased with 5% of the original activity remaining after 14 days at pH 10.7.

Figure 10:
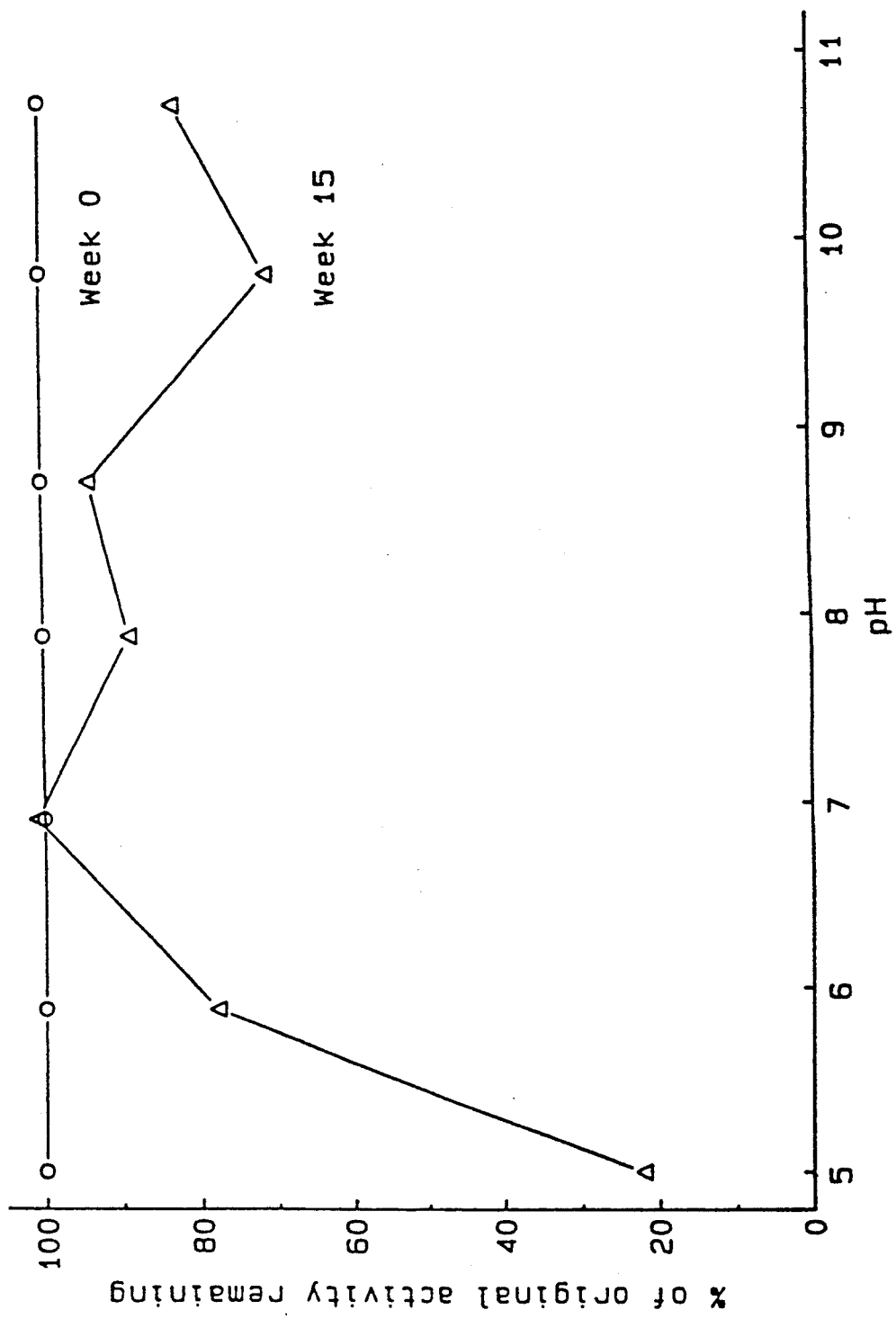

Protease 2 The results are shown in FIG. 10.

Protease 2 is more stable than Protease 1. The enzyme was most unstable at pHs below 7 or above 9 after 15 weeks. At pH 7, no loss in activity was detected after 15 weeks.

Stability at Ambient Temperature

Figure 11:
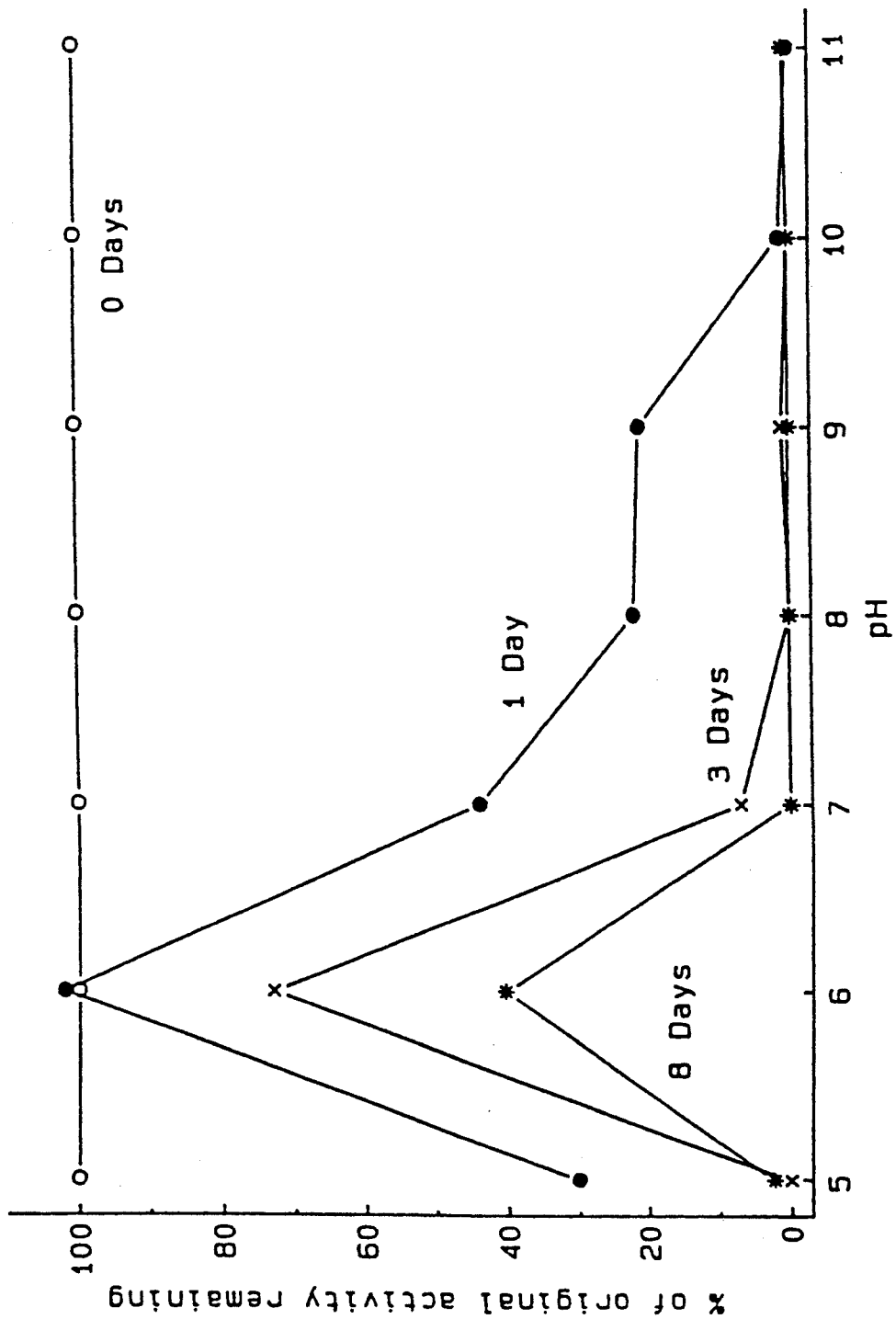
FIGS. 11 and 12 show the pH stability of Protease 1 and Protease 2 respectively at ambient temperature.

Protease 1 The results are shown in FIG. 11.

Protease 1 is not very stable except at pH 6 where 40% of the original activity remained after 8 days.

Figure 12:
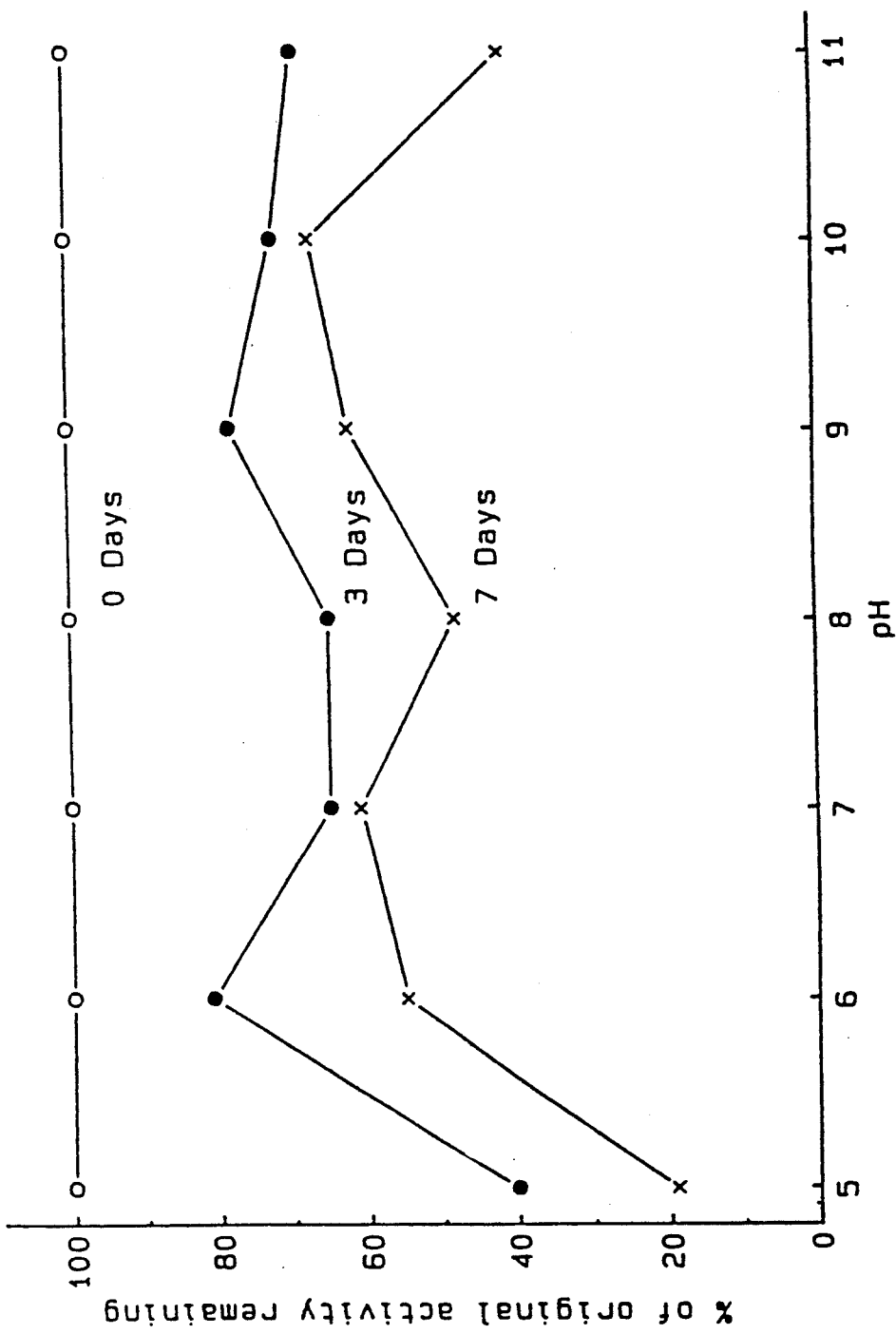

Protease 2 The results are shown in FIG. 12.

Protease 2 is more stable than Protease 1, with greatest stability being detected at pHs between 6 and 10, where 50% of the original activity remained after 7 days.

The Effect of NaCl on the Callus-Degrading Activities of Protease 1 and Protease 2

Proteases 1 and 2 were assayed using the quantitative callus-degrading assays.

Figure 13:
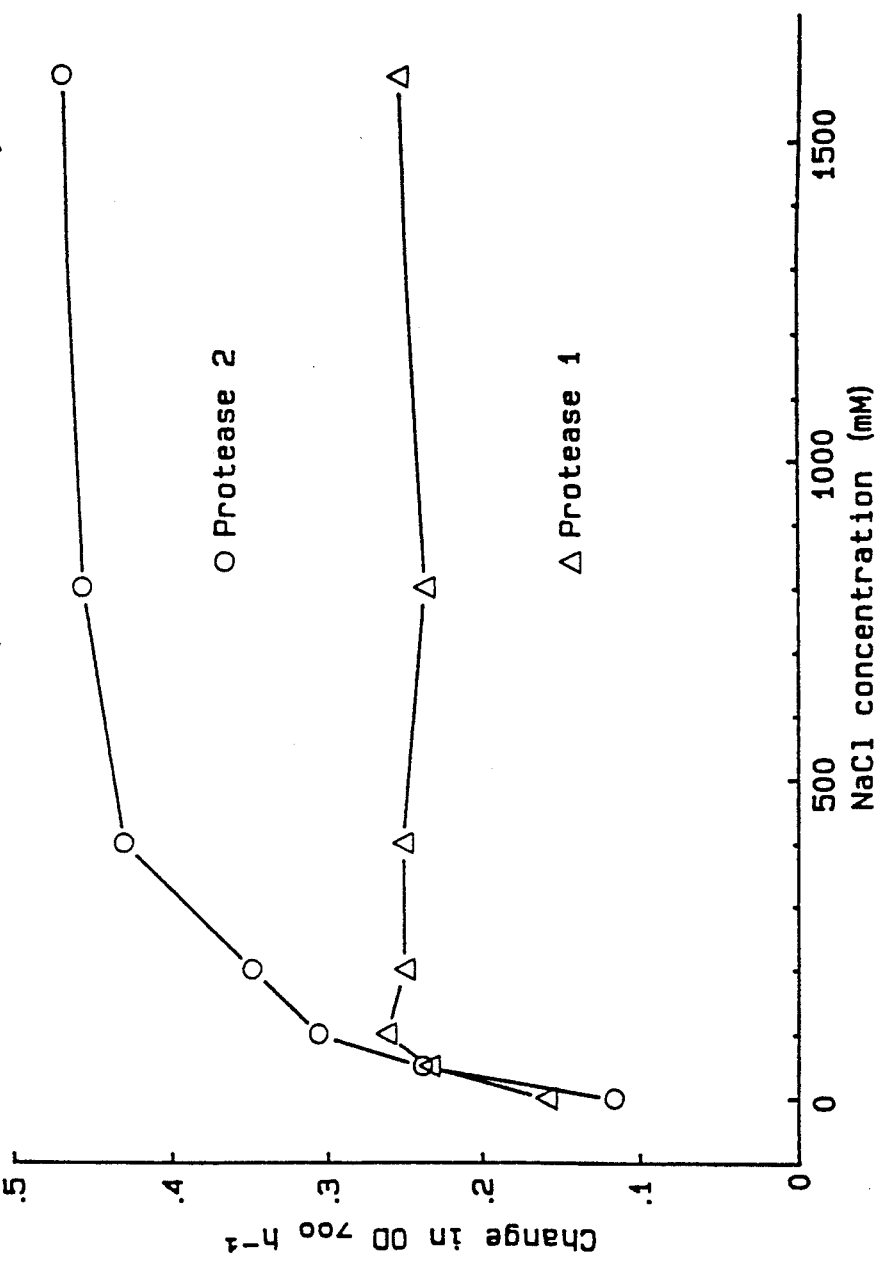
FIG. 13 shows the effect of NaCl on the callus-degrading activities of Proteases 1 and 2.

Protease 1 (4.5 Protease Units) was incubated at 40° C. in 150 mM Tris-HCl (pH 7.1) containing different concentrations of NaCl (0-1.6M). The results are shown in FIG. 13. Maximum callus-degrading activity, 1.7-fold higher than with no NaCl, was detected at a concentration of 100 mM NaCl.

Protease 2 (88.2 Protease Units) was incubated at 50° C. in 150 mM Tris-HCl (pH 7.5) containing different concentrations of NaCl (0-1.6m). The results are shown in FIG. 13. Maximum callus-degrading activity, 4.5-fold higher than with no NaCl, was detected at a concentration of 1.6M NaCl. The callus-degrading activity of Protease 2 is, therefore, more affected by NaCl or ionic strength than that of Protease 1.

The Effect of Ionic Strength and Various Ions on Callus-Degrading Activities of Proteases 1 and 2

To determine whether ionic strength and/or specific ions were stimulatory to callus-degrading activity, the effect of various compounds was investigated. The quantitative callus-degrading assay was used with assay buffers containing LiCl, NaCl, KCl, CsCl (ionic strength 0.1M), $Na_2SO_4$, $MgCl_2$, $CaCl_2$ (ionic strength 0.3M) or no additional salts. The presence of 10 mM EDTA, which chelates divalent ions present in the callus substrate, was also investigated.

Figure 14:
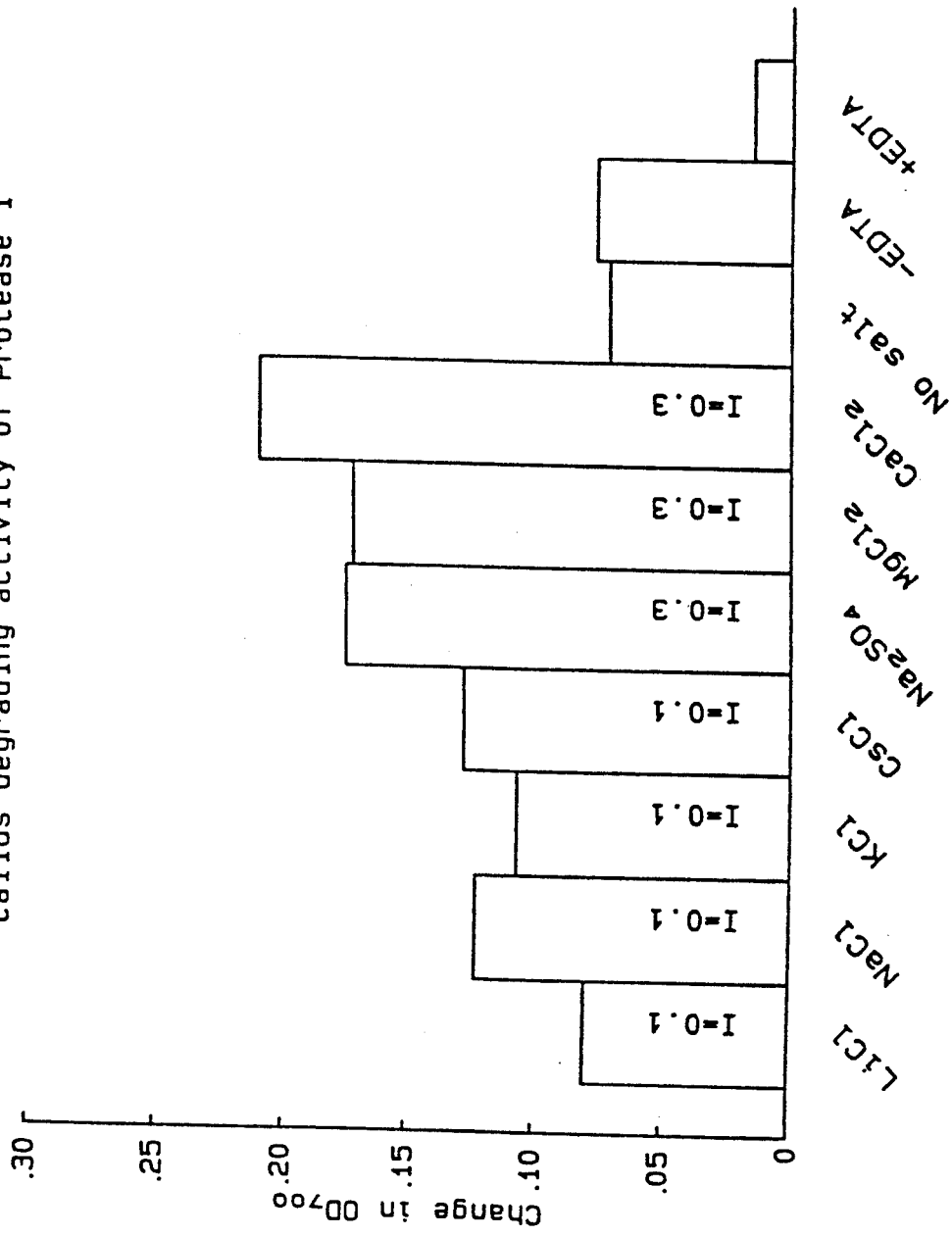
FIGS. 14 and 15 show the effect of ionic strength and ionic species on the callus-degrading activity of Proteases 1 and 2 respectively.

Protease 1 (3 Protease Units) was incubated at 40° C. in 150 mM Tris-HCl (pH 7.1) containing the required compound. The results are shown in FIG. 14. The addition of monovalent ions (ionic strength 0.1M) had little effect on callus-degrading activity. At an ionic strength of 0.3M, the activity was increased and this was not dependent on any particular ionic species. Callus-degrading activity was decreased in the presence of 10 mM EDTA indicating that small quantities of divalent ions in the substrate increased Protease 1 activity.

Figure 15:
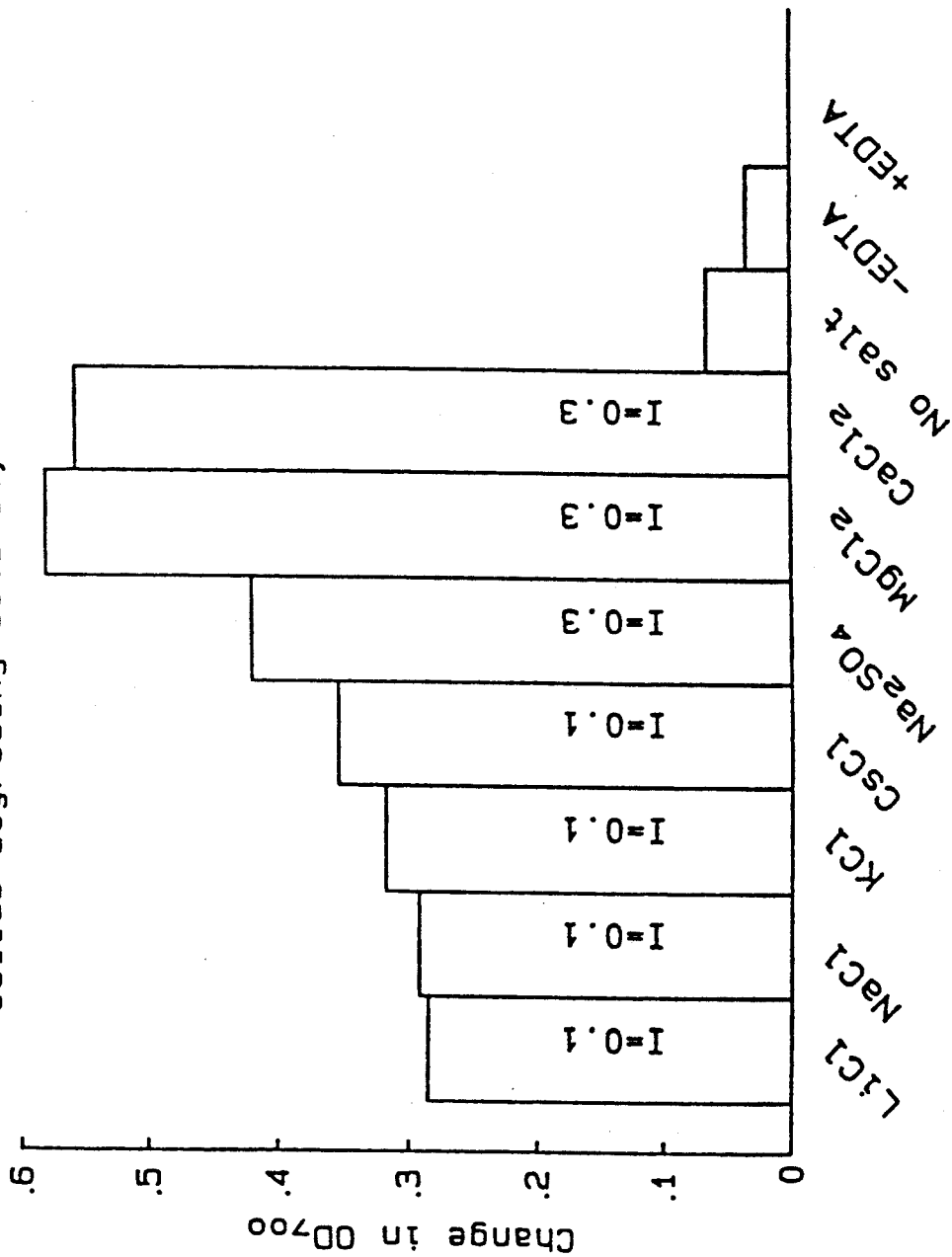

Protease 2 (88.2 Protease Units) was incubated at 50° C. in 150 mM Tris-HCl (pH 7.5) containing the required compound. The results are shown in FIG. 15. The addition of monovalent ions (ionic strength 0.1M) greatly increased the callus-degrading activity with $Na_2SO_4$ (ionic strength 0.3M), the activity was increased further. Higher activities were detected in the presence of $MgCl_2$ and $CaCl_2$ (ionic strength 0.3M). In the presence of 10 mM EDTA, no activity was detected.

Protease 2 is, therefore, affected to a greater extent than Protease 1 by the ionic strength of the environment and by divalent ions.

The Effect of $MgCl_2$ on Callus-Degrading Activities of Proteases 1 and 2

Proteases 1 and 2 callus-degrading activities were determined using the quantitative assays.

Figure 16:
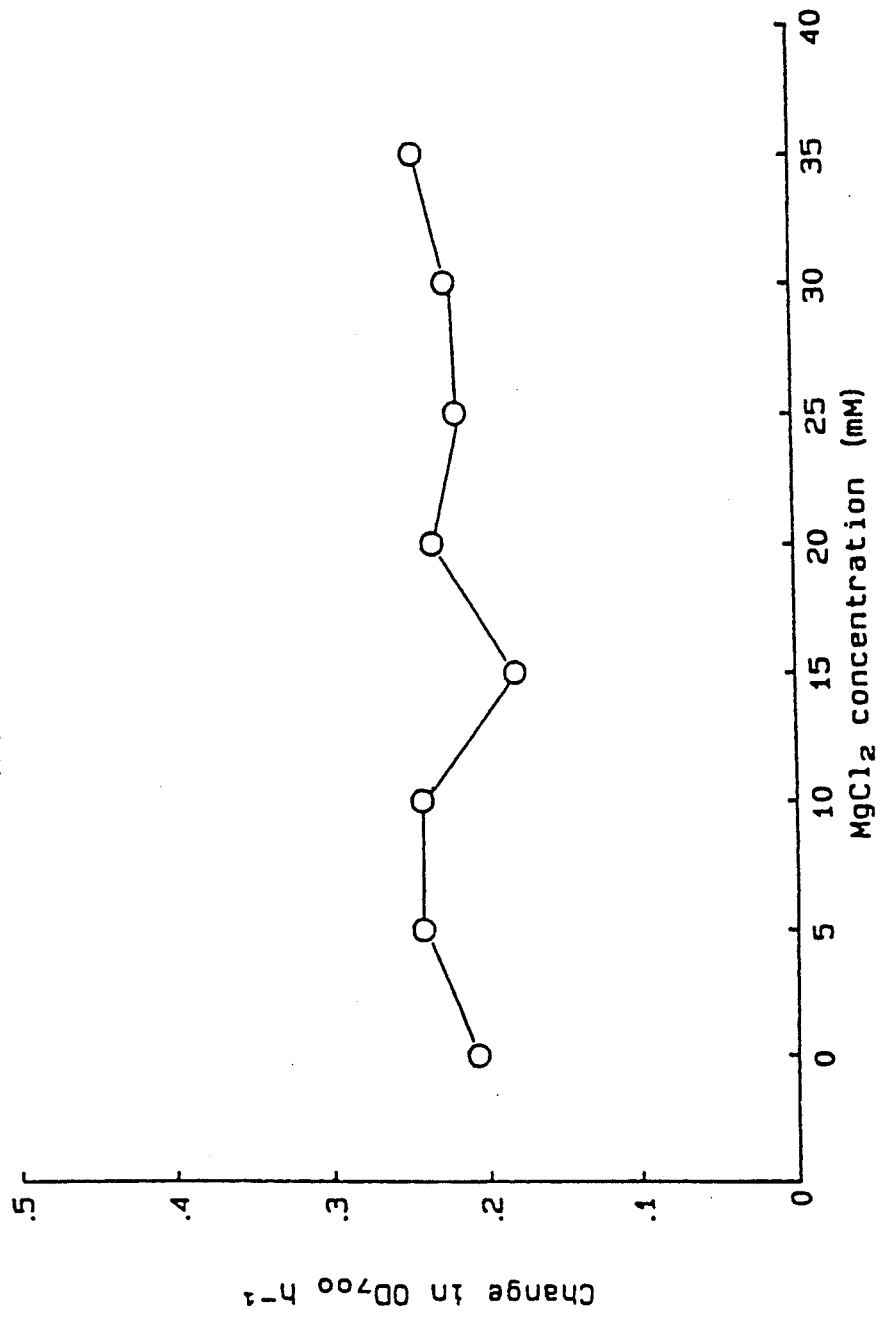
FIGS. 16 and 17 show the effect of $MgCl_2$ on the callus-degrading activity of Proteases 1 and 2 respectively.

Protease 1 (4.5 Protease Units) was incubated at 40° C. in 150 mM Tris-HCl (pH 7.1) containing different concentrations of $MgCl_2$ (0-35 mM). Protease 1 was also assayed in buffer containing 45 mM NaCl. The results are shown in FIG. 16. There was a slight increase in callus-degrading activity in the presence and absence of 5 mM $MgCl_2$ compared to the control which contained no $MgCl_2$. The activity in the presence of 45 mM NaCl was equivalent to that at 15 mM $MgCl_2$ (data not shown).

Figure 17:
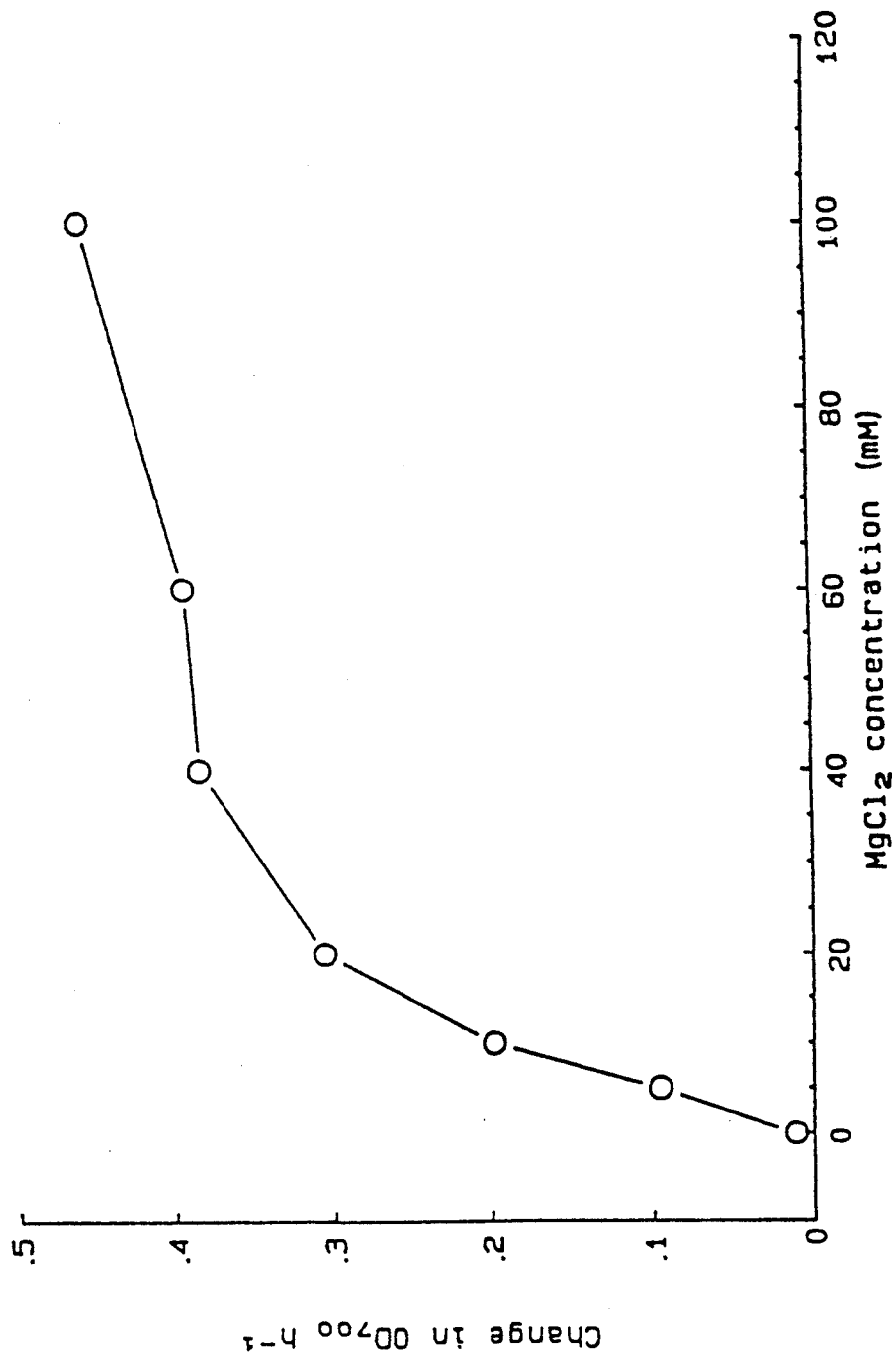

Protease 2 (31.5 Protease Units) was incubated at 50° C. in 150 mM and Tris-HCl (pH 7.5) containing different concentrations of $MgCl_2$ (0-100 mM). Protease 2 was also assayed in buffer containing 60 mM NaCl. The results are shown in FIG. 17. The callus-degrading activity of Protease 2 increased with increasing concentrations of $MgCl_2$. The activity in the presence of $MgCl_2$ was 4.7-fold higher than that in NaCl at an equivalent ionic strength.

The callus-degrading activity of Protease 2 in contrast to that of Protease 1, is greatly stimulated by high ionic strengths and by $MgCl_2$.

Demonstration of Keratinase Activity

Extraction of Keratin from Finely Ground Callus

Finely ground callus (0.4 g) was added to 25 ml extraction buffer which comprised 50 mM Tris-HCl (pH 7.2), 6M urea and 2% (v/v) B-mercaptoethanol. The suspension was homogenized using an Ultra-Turrax homogenizer (TP18/10, Janke & Kunkel) at full speed for 2 minutes, before and after stirring at 4° C. for 20 h. The suspension was centrifuged at 50,000 g for 30 minutes at 4° C. and the resulting supernatant fluid was dialyzed three times against 4 liters CASC buffer (0.1M sodium citrate adjusted to pH 2.65 with 0.1M citric acid) over a 24 hour period.

The dialyzed fluid was centrifuged as previously and the supernatant fluid containing the keratin was transferred to a fresh centrifuge tube. The pH was adjusted to 4.0 with 1M NaOH and the resulting suspension was centrifuged at 4000 g for 2 minutes.

The keratin-containing pellet was resuspended in 1 ml CASC buffer and the pH was adjusted to 4.0 with 1M NaOH. The suspension was centrifuged (4000 g, 2 minutes) and the pellet resuspended in 1 ml CASC buffer. The pH was adjusted to 4.0 and the suspension centrifuged (4000 g, 2 minutes). The pellet was resuspended in 1 ml CASC buffer and aliquots of the keratin solution were stored at −20° C. The concentration of the keratin was approximately 7 mg ml$^{-1}$ according to dry weight determinations.

Keratin Degradation by Proteases 1 and 2 and Crude Amicon Retentate

Figure 18A:
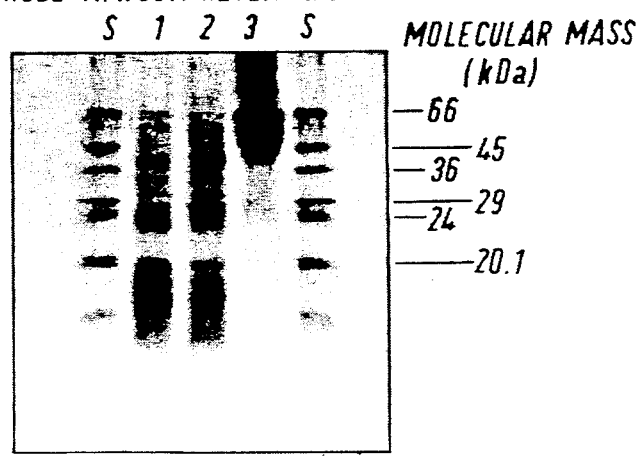
FIG. 18a shows the degradation of keratin by Protease 1 and crude Amicon retentate.
Figure 18B:
FIG. 18b shows the degradation of keratin by doubling dilutions of Protease 2.

NaOH (25 μl, 0.5M) and 50 μl Tris-HCl (0.3M, pH 8.0) were added to 50 μl keratin solution to adjust its pH to 8. 25 μl concentrated crude Amicon retentate (as obtained in the above process) or Protease 1 (2.4 Protease Units) were incubated with the adjusted keratin solution at 40° C. for 1.5 h. Protease 2 (3.0 Protease Units) was diluted in 100 mM Tris-HCl (pH 8.0) from N to N/1024 (doubling dilutions). 25 μl of each dilution was incubated with the adjusted keratin solution at 48° C. for 10 minutes. At the end of the incubation period, double strength SDS-PAGE loading buffer (150 μl) was added to each reaction mixture. The samples were boiled for 2 minutes and 2 μl of each sample was applied to an SDS-PAGE gel. The results are shown in FIGS. 18a and 18b.

The high molecular mass keratin polypeptides (45–66 kDa) were degraded by Protease 1 and Protease 2 and by the enzymes in the Crude Amicon retentate, as indicated by the presence of smaller degradation products (>36 kDa) after incubation with the enzymes. This indicates that both Protease 1 and Protease 2 possess keratinase activity.

Demonstration of Activity Against Other Substrates

Chicken Feathers

Chicken down feathers were rinsed three times in distilled water. Crude Amicon retentate was freeze-dried and reconstituted in 150 mM sodium phosphate buffer (pH 8.0) containing 0.05% (w/v) sodium azide at a concentration of 100,000 Protease Units ml$^{-1}$, 200 μl of this was incubated with an intact down feather at 50° C. After 18 h, the barbs of the feather had detached from the shaft.

Collagenase Activity

Agarose (0.3 g) was dissolved in 50 ml Tris-HCl buffer (pH 7.5, 150 mM) and cooled to 50° C. 1 ml volumes of agarose containing 3.5% (w/v) collagen were poured into 1.5×1.5 cm moulds and allowed to set.

Crude Amicon retentate (as obtained above) was freeze-dried and reconstituted in 150 ml Tris-HCl (pH 7.5), and 10 μl (514 Protease Units) was applied to the surface of the collagen gel. Control, comprising 150 mM Tris-HCl (pH 7.5) was applied to a second gel. The gels were incubated at 37° C. After 4 days incubation with the enzyme, the collagen pieces appeared to be reduced in size compared to the control.

Protease-containing compositions of the present invention, and pharmaceutically acceptable formulations thereof, can be used as agents to degrade natural proteinaceous material especially for the purposes of treating medical conditions. Protease-containing compositions of the present invention, and pharmaceutically acceptable formulations thereof, have, as previously mentioned, the ability to degrade in vitro human callus obtained from the skin and can be used as degrading agents for treating corns and calluses, for example, on the feet in vivo. Preferably the compositions of the invention are in the form of pharmaceutical preparations for topical application such as solutions, creams, ointments, ointment sticks, gels, powders or adhesive plasters. Such topical compositions may contain other active ingredients such as antibiotics or fungicides, a swell as, conventional additives for such compositions. The proteases of the present invention, and formulations thereof, can also be used in other applications where it is desired to degrade or digest proteinaceous material, modify proteinaceous raw materials or produce useful protein degradation products. These applications include for example: cleansing surfaces of proteinaceous material including contact lenses; cleansing textiles and the like; food processing; and de-hairing of animal hides.

While various embodiments of the present invention have been described in detail, it is apparent that modifications and adaptations will occur to those skilled in the art. However, it is to be expressly understood that such modifications and adaptations are within the spirit and scope of the present invention, as set forth in the following claims.

I claim:

1. An isolated enzyme material having protease activity obtained from *Micrococcus sedentarius* having the following characteristics:
   (a) water-soluble,
   (b) non-dialyzable through a membrane having a molecular weight cut-off of 10 kDa,
   (c) an isoelectric point of about 4.6,
   (d) a molecular weight of 30.3 kDA,
   (e) an optimum pH for protease activity at about 8.2 and an optimum temperature for protease activity at about 40° C.

2. The isolated enzyme material of claim 1 obtained from *Micrococcus sedentarius* NCIBM 40287.

3. The isolated enzyme material of claim 1 having an optimum pH for human callus-degrading activity of about pH 7.1 and an optimum temperature of about 40° C.

4. The isolated enzyme material of claim 1 wherein said enzyme material is in a substantially pure form.

5. The isolated enzyme material of claim 1 wherein said enzyme material is in the form of a cell-free culture of *Micrococcus sedentarius*.

6. The isolated enzyme material of claim 1, in a pharmaceutical composition comprising the enzyme material and a pharmaceutically acceptable carrier or excipient.

7. The isolated enzyme material of claim 1, in a composition for topical application to the skin of a human subject comprising the enzyme material and a topically acceptable base.

8. An isolated enzyme material having protease activity obtained from *Micrococcus sedentarius* having the following characteristics:
   (a) water-soluble,
   (b) non-dialyzable through a membrane having a molecular weight cut-off of about 10 kDa,
   (c) an isoelectric point of 2.7,
   (d) a molecular weight of 50 kDa,
   (e) an optimum pH for protease activity at about 10.2 and an optimum temperature for protease activity at about 46° C.

9. The isolated enzyme material of claim 8 obtained from *Micrococcus sedentarius* NCIMB 40287.

10. An isolated material of claim 8 wherein said enzyme material is in a substantially pure form.

11. The isolated enzyme material of claim 8 wherein said enzyme material is in the form of a cell-free culture of *Micrococcus sedentarius*.

12. The isolated enzyme material of claim 8 having an optimum pH for human callus degrading activity at about 7.5 and an optimum temperature at about 50° C.

13. The isolated enzyme material of claim 8, in a pharmaceutical composition comprising the enzyme material and a pharmaceutically acceptable carrier or expedient.

14. The isolated enzyme material of claim 8, in a composition for topical application to the skin of a human subject comprising the enzyme material and a topically acceptable base.

* * * * *